United States Patent
Yamada et al.

(10) Patent No.: US 6,270,483 B1
(45) Date of Patent: Aug. 7, 2001

(54) LIQUID DISCHARGE REGULATOR AND LIQUID FEEDER EQUIPPED WITH THE SAME

(75) Inventors: Keiichi Yamada, Kaizuka; Mitsuyoshi Inoue, Kashiba; Hajime Nakazawa; Atsushi Yamamoto, both of Osaka; Tatsuji Higashi, Izumisano, all of (JP)

(73) Assignee: Daiken Iki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/296,536

(22) Filed: Apr. 22, 1999

(30) Foreign Application Priority Data

Jul. 3, 1998 (JP) .................................................. 10-188965
Jul. 3, 1998 (JP) .................................................. 10-188966
Jul. 3, 1998 (JP) .................................................. 10-188967

(51) Int. Cl.[7] ...................................................... A61M 5/00
(52) U.S. Cl. ............................ 604/249; 604/9; 604/246; 137/512.1; 137/109
(58) Field of Search ................................. 604/246.2, 248, 604/249, 30, 32, 33, 48, 8–10; 137/109, 110, 512.1, 493, 833

(56) References Cited

U.S. PATENT DOCUMENTS

| | | |
|---|---|---|
| 2,323,115 | 6/1943 | Bryant . |
| 3,785,616 | 1/1974 | Moore . |
| 3,951,147 | 4/1976 | Tucker et al. . |
| 4,497,768 | 2/1985 | Hubbard et al. . |
| 4,509,946 | 4/1985 | McFarlane . |
| 4,634,434 | * 1/1987 | Marino, Jr. et al. ................ 604/246 |
| 4,953,594 | 9/1990 | Von Berg . |
| 5,101,854 | * 4/1992 | Bron ...................................... 137/501 |
| 5,113,904 | 5/1992 | Aslanian . |
| 5,807,337 | 9/1998 | Yamada et al. ..................... 604/143 |
| 6,126,628 | * 10/2000 | Nissels ..................................... 604/9 |

FOREIGN PATENT DOCUMENTS

| | | |
|---|---|---|
| 0271785 | 6/1988 | (EP) . |
| 0369712 | 5/1990 | (EP) . |
| 57-203451 | 12/1982 | (JP) . |
| 61-45946 | 3/1986 | (JP) . |
| 62-501820 | 7/1987 | (JP) . |
| 63-74570 | 5/1988 | (JP) . |
| 2-11160 | 1/1990 | (JP) . |
| 2-180274 | 7/1990 | (JP) . |
| 2-307477 | 12/1990 | (JP) . |
| 3-118071 | 5/1991 | (JP) . |
| 3-218772 | 9/1991 | (JP) . |
| 4-18541 | 2/1992 | (JP) . |
| 8-68383 | 3/1996 | (JP) . |
| 9-225028 | 9/1997 | (JP) . |
| 9225028 | 9/1997 | (JP) . |
| 86/04821 | 8/1986 | (WO) . |
| 95/02877 | 1/1995 | (WO) . |

* cited by examiner

Primary Examiner—Anhtuan T. Nguyen
Assistant Examiner—Jennifer Maynard
(74) Attorney, Agent, or Firm—Smith Patent Office

(57) ABSTRACT

A compact liquid discharge regulator is provided at low cost by arranging a channel spirally formed in the surf ace of a passage forming member. The surface of the passage forming member is brought into close contact with the inner surface of a housing part, and the channel functions as a liquid passage. In this construction, the sectional form and length of the channel can be formed at high precision in accordance with the design. Therefore, a desired pipe loss is obtainable only by designing in advance the sectional form and length of the channel so as to correspond to the pipe loss. Particularly, with injection molding, mass production of a passage forming member of identical pipe loss can be effected merely by preparing a mold corresponding to the pipe loss, thus leading to a considerable reduction in the manufacturing cost of the discharge regulator.

11 Claims, 17 Drawing Sheets

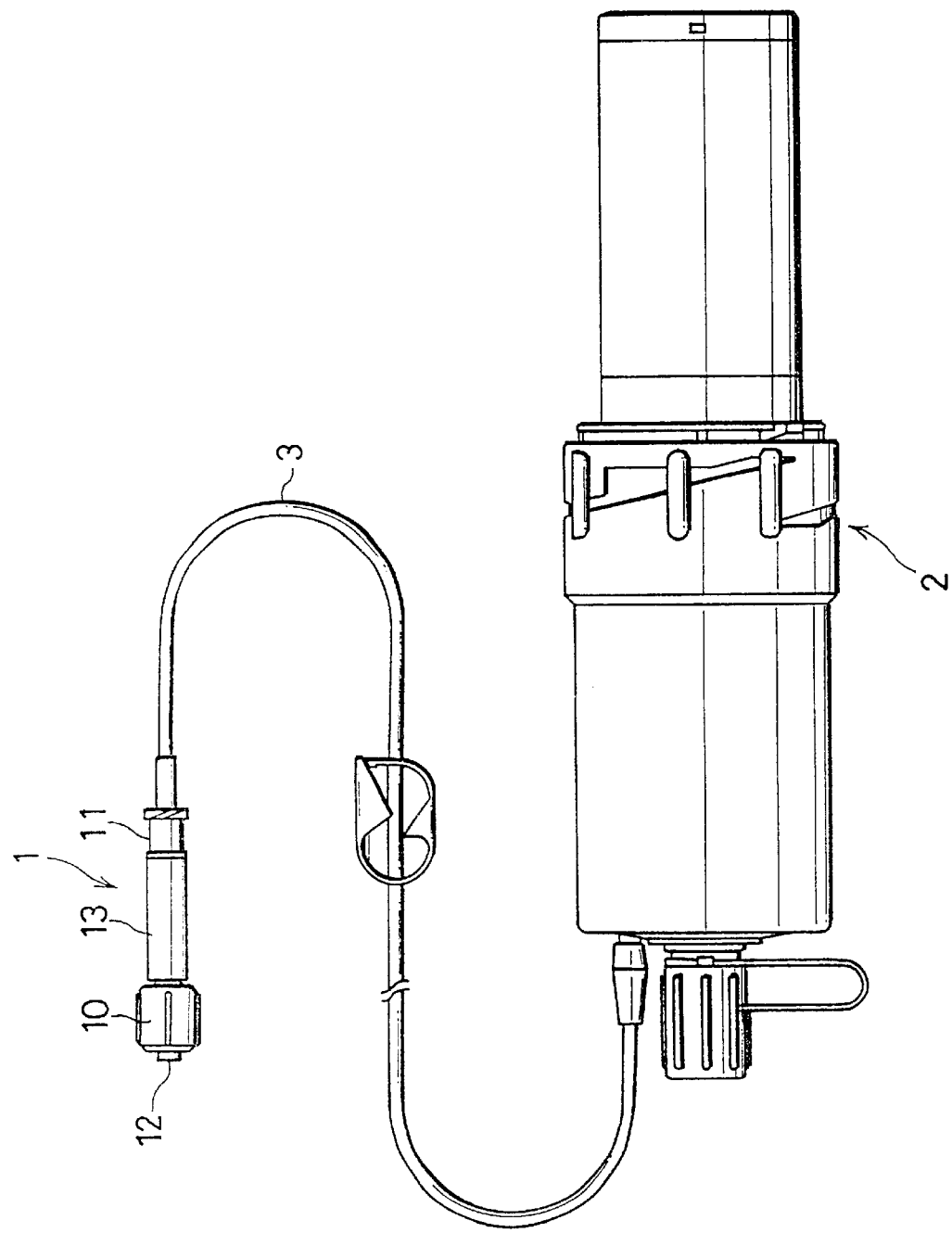

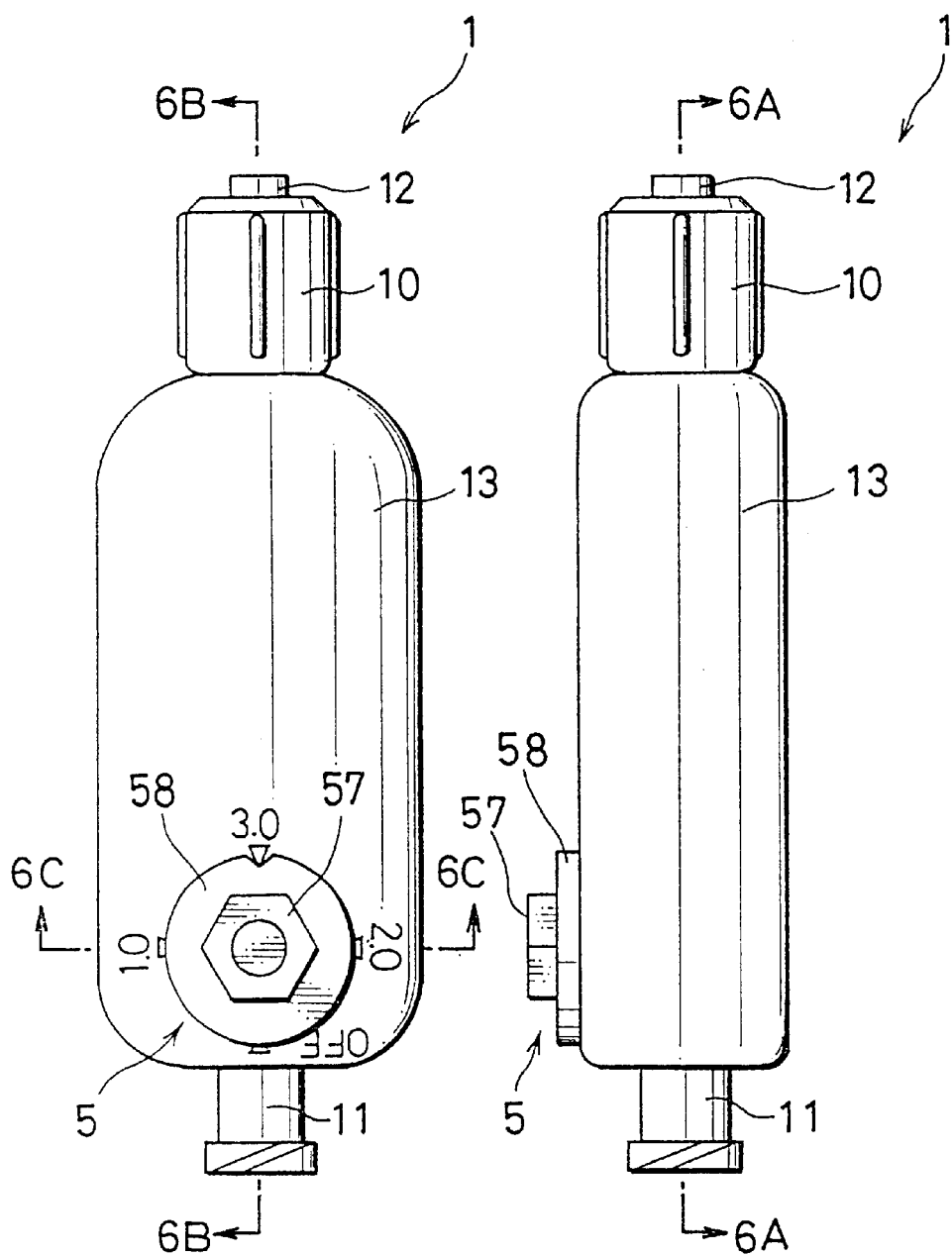

| ROTATION ANGLE | CONNECTED STATE | DISCHARGE |
|---|---|---|
| 0° | | OFF |
| 90° | | R$_B$ |
| 180° | | R$_A$ + R$_B$ |
| 270° | | R$_A$ |

FIG. 9A
FIG. 9B
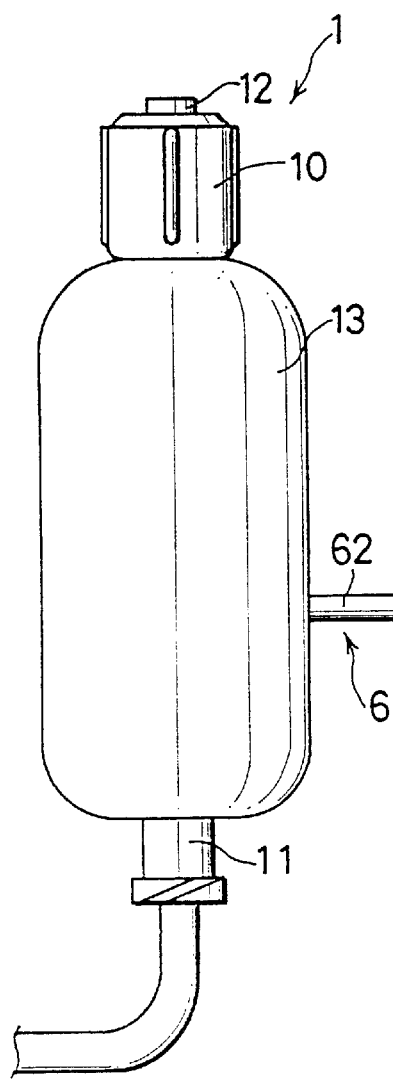
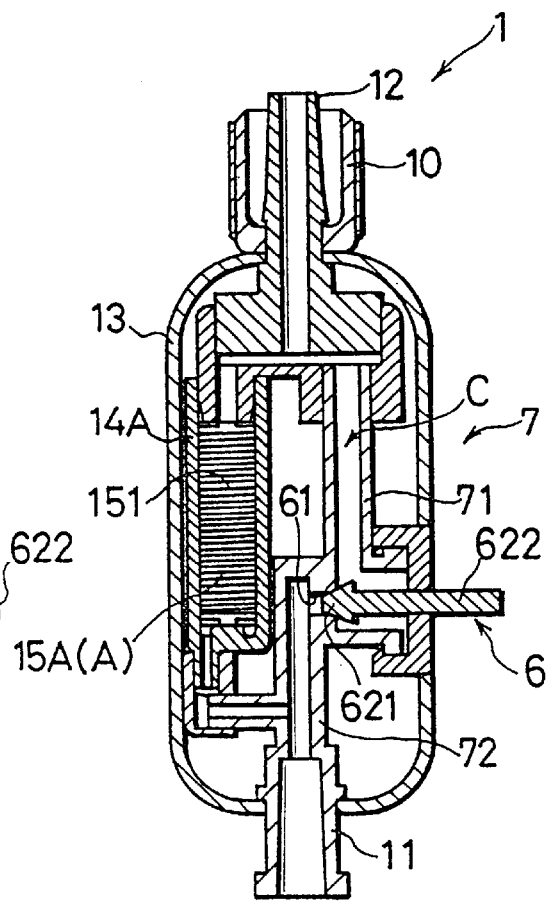

FIG. 10A
FIG. 10B
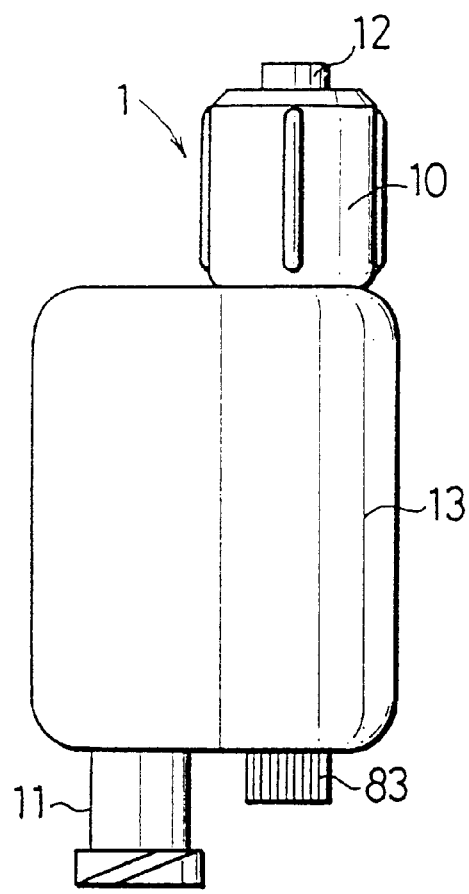
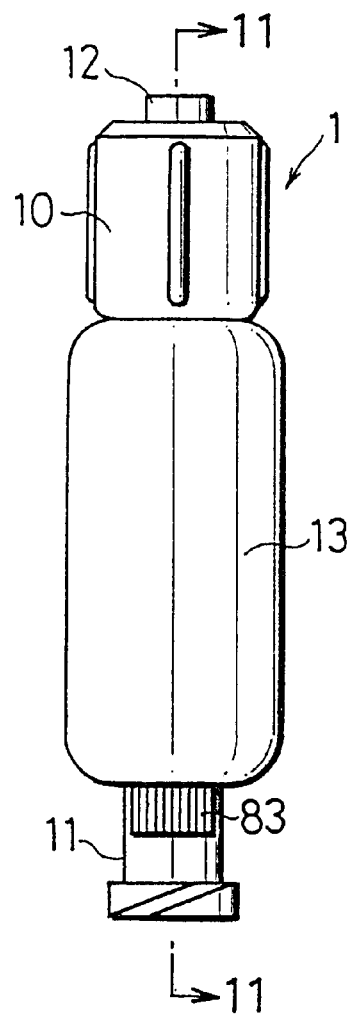

LIQUID DISCHARGE REGULATOR AND LIQUID FEEDER EQUIPPED WITH THE SAME

BACKGROUND OF THE INVENTION

1. Field of the Invention

The invention relates to liquid discharge regulators and liquid feeders for use in the medical field and the like.

Description of the Prior Art

Presently, a combination of a liquid feeder and a discharge regulator is employed to inject chemical liquids, such as antibiotics and anti-cancer drugs, into the patient's body in portions, e.g., several cubic centimeters per hour, over a long period of time. Examples of the liquid feeder are power syringe pumps, balloon infusers, and an apparatus described in the International Publication No. WO95/28977. One of the examples of the discharge regulator is described in Japanese Unexamined Patent Publication No. 9-225028 (1997). In this discharge regulator, an inlet part and an outlet part project from a casing. The inlet part is connected to a liquid feeder through a tube, and the outlet part is connected to a body connecting tube. With this construction, the liquid stored in the liquid feeder is controlled as to discharge by the discharge regulator while being injected into the body over a long period of time.

In the casing of the discharge regulator there are provided two tubes of fine (small) diameter with the same diameter and different lengths which are made of polyvinyl chloride or the like. One end of each tube is connected to the inlet part via a passage branching part, and the other end is connected to the outlet part. Thereby each tube functions as a liquid passage from the inlet part to the outlet part. A control stopper is attached to the passage branching part and it is arranged such that the liquid that has reached via the inlet part can selectively flow through a plurality of tubes of fine diameter by operating the control stopper. Therefore, the plural tubes thus arranged have different pipe losses and, by selectively changing the liquid passage with the control stopper, the discharge of the liquid flowing through the outlet part can be switched to the following three stages:

i) a first discharge obtained by injecting a liquid only through one of the tubes of fine diameter (the discharge in accordance with the pipe loss of one said tube);

ii) a second discharge obtained by injecting a liquid only through the other tube (the discharge in accordance with the pipe loss of the other said tube); and iii) a third discharge obtained by injecting a liquid through both tubes (the sum of the first and second discharges).

Here, the pipe loss of a passage is determined by inside diameter and length. In the above discharge regulator, the tubes of fine diameter form a passage and their lengths are adjusted to set the pipe losses at a suitable value so as to control the discharge. Unfortunately, the inside diameter of tubes of fine diameter is subject to a certain degree of variation. Therefore, if a tube of fine diameter with a length corresponding to a predetermined pipe loss is used as it is, the desired pipe loss may not be always obtained. To this end, the following operations are performed to set a desired pipe loss. Firstly, a tube of fine diameter having a length corresponding to the pipe loss is prepared and a liquid is actually allowed to flow to measure its pipe loss (flow rate), thereby inspecting whether it is a predetermined value or not. As a result, when the obtained value deviates from the predetermined value, the length of the tube is altered and its pipe loss is measured to check whether it is the predetermined value or not. It is necessary to repeat these operations with respect to each passage. This results in one of the factors which can increase the cost of manufacture.

There is an idea of suppressing the variation in the inside diameters of tubes of fine diameter by relatively increasing the inside diameter. In this case, to obtain a predetermined pipe loss, it is necessary to increase the length of a tube of fine diameter as its inside diameter increases. This increases the size of discharge regulators. In addition, when a tube of fine diameter is housed in a casing, the tube might get bent to cause poor or no flow of liquid.

The above discharge regulator provides a three-stage switching of discharge. It is, however, desired a continuous discharge regulation to effect fine adjustment in response to the change of patient s condition and the efficacy of chemical liquids. Unfortunately, the continuous discharge cannot be effected by the conventional discharge regulators.

Although the conventional discharge regulators cannot perform continuous discharge regulation, it is possible to approach this regulation by arranging such that the discharge is switched to more stages by having more tubes of fine diameter of different pipe losses. However, in the conventional discharge regulators which require a great number of tubes of fine diameter with an attempt to the continuous discharge regulation, the cost of device increases as the number of tubes of fine diameter increases. In addition, an increase in the number of tubes increases the size of device.

Further, in the prior art, a liquid feeder and a discharge regulator are separately and independently provided, and connected by a tube. Therefore, to inject a liquid in portions into the patient's body over a long period of time, a great number of component parts are needed, which results in one of the factors increasing the cost of liquid injection. In addition, it is necessary to prepare a liquid feeder and a discharge regulator and then connect them by a tube each time a liquid injection is made. This lowers the operating performance of liquid injection.

SUMMARY OF THE INVENTION

It is an object of the present invention to provide a liquid discharge regulator and a liquid feeder which have overcome the above problems residing in the prior art.

According to an aspect of the invention, a liquid discharge regulator comprises: a casing having a liquid inlet part and a liquid outlet part; and a passage forming member formed with a channel in a surface thereof, the surface of the passage forming member coming into contact with an inner surface of the casing to define a passage for introducing a liquid from the inlet part to the outlet part and to regulate the discharge of the liquid from the outlet part.

According to another aspect of the invention, a liquid feeder comprises: a main body including an outlet part in one end of the main body, the outlet part having an outlet for discharging a liquid stored in the main body, and a discharge regulation section provided in the outlet part for introducing the liquid from the main body to the outlet to regulate the discharge of the liquid.

These and other objects, features and advantages of the present invention will become more apparent upon reading of the following detailed description and accompanying drawings.

BRIEF DESCRIPTION OF THE DRAWINGS

FIG. 2 is a diagram showing a situation where the above discharge regulator is put into service;

FIGS. 5A and 5B are diagrams of a liquid discharge regulator according to a second preferred embodiment of the invention;

FIGS. 9A and 9B are diagrams of a liquid discharge regulator according to a third preferred embodiment of the invention;

FIGS. 10A and 10B are diagrams of a liquid discharge regulator according to a fourth preferred embodiment of the invention;

DETAILED DESCRIPTION OF THE PREFERRED EMBODIMENTS

The invention relates to a liquid discharge regulator and a liquid feeder incorporating a discharge regulator which are used in the medical field and the like. A description of preferred embodiments of the liquid discharge regulator will be presented prior to the description of preferred embodiment of the liquid feeder.

Liquid Discharge Regulators

A. First Preferred Embodiment

Figure 1A:
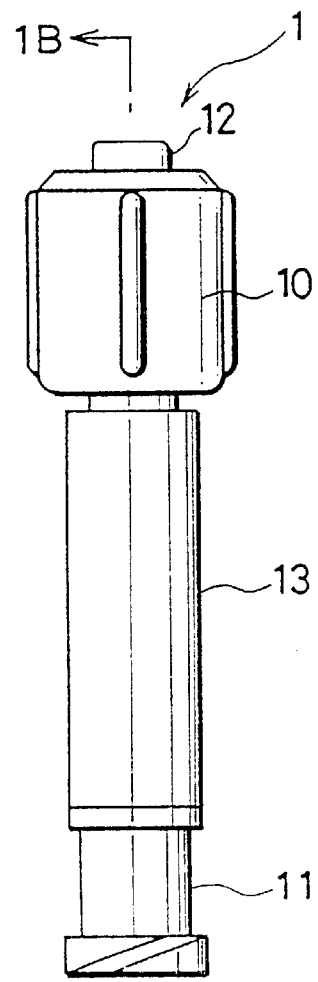
FIGS. 1A to 1C are diagrams of a liquid discharge regulator according to a first preferred embodiment of the invention.
Figure 1B:
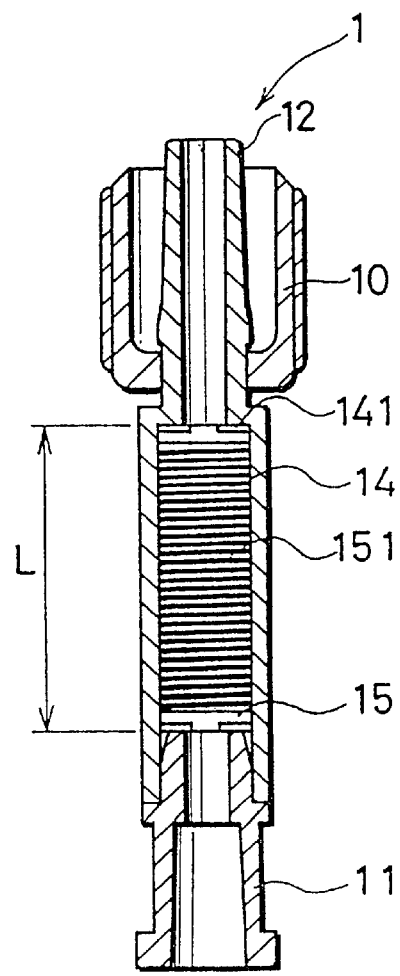
Figure 1C:
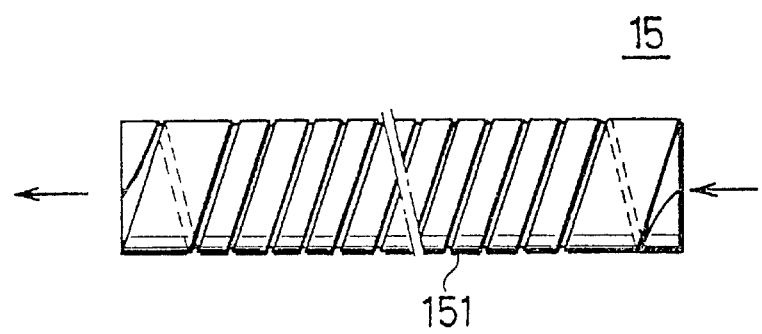

FIGS. 1A to 1C are diagrams of a first preferred embodiment of a liquid discharge regulator according to the invention. FIG. 2 is a situation where the discharge regulator of FIGS. 1A to 1C is placed in service. A discharge regulator 1 is used in combination with a liquid feeder 2. That is, a tube 3 extending from the liquid feeder 2 is connected to an inlet part of the discharge regulator 1, and another tube (not shown) to be connected to the body is connected to an outlet part 12. It is therefore possible to inject a liquid in portions into the body over a long period of time.

Referring to FIG. 1B, in the discharge regulator 1, a housing part 14 is disposed almost centrally of a casing 13 to define a columnar housing space. A columnar passage forming member 15 is brought into engagement with the housing space of the housing part 14 from one end of the casing 13 (the lower side as seen in FIG. 1B), and the distal end of the member 15 is engaged to a step portion 141 of the housing part 14. Thus, with the passage forming member 15 housed in the housing part 14, an inlet part 11 is inserted into one said end of the casing 13, so that the rear end of the passage forming member 15 is engaged to the distal end of the inlet part 11. Thereby, the passage forming member 15 is housed and secured to the housing part 14 of the casing 13.

The passage forming member 15 is made of a resin material, e.g., plastic. As shown in FIG. 1C, a channel 151 having a rectangular, triangular or semicircular sectional form is spirally provided in the surface of the passage forming member 15. The outside diameter of the member 15 is the same or slightly larger than the inside diameter of the housing part 14. When the passage forming member 15 engages the housing part 14 in the above manner, its surface is brought into close contact with the inner surface of the casing 13 (the housing part 14). Thus, a liquid runs in the housing part 14 via the inlet part 11 and then goes to the other end (the upper side as seen in FIG. 1C) of the casing 13 through the channel 151, which functions as a liquid passage.

Disposed at the other end of the casing 13 is an outlet part 12 integrally formed with the casing 13. The liquid that has reached through the channel 15 flows through the outlet part 12. In FIGS. 1A and 1B, reference numeral 10 designates a lock part by which a body connecting tube (not shown) attached to the outlet part 12 is fastened and locked against the outlet part 12.

As stated above, in the discharge regulator 11 according to this embodiment, the channel 151 provided spirally in the surface of the passage forming member 15 functions as a liquid passage, thus producing the following effects. Specifically, a well known manner, e.g., injection molding, can be used in manufacturing the passage forming member 15 of plastic which has a channel 151 in its surface, and the sectional form and length of the channel 151 can be formed at high precision in accordance with the design. Hence, a desired pipe loss is obtained at a time by designing in advance the sectional form and length of the channel 151 so as to accord the pipe loss. Particularly, with injection molding, mass production of the passage forming member 15 of the same pipe loss can be effected only by preparing a mold according to the pipe loss. This leads to a considerable reduction in the manufacturing cost of the discharge regulator 1.

In addition, the channel 151 serving as a passage is spirally provided in the surface of the passage forming member 15 such that the channel 151 is sufficiently longer than the whole length L of the passage forming member 15 (see FIG. LB). Therefore, the sectional area of the channel 151 can be increased by an amount to ensure sufficient length. This results in the effect that the passage (the channel 151) hardly becomes clogged. Also, a greater sectional area of the channel 151 further facilitates the molding of the channel forming member 15 and further improves the precision.

Since the channel 151 functions as a passage, passages can be concentrated at a narrow region. This leads to a compact device, as compared to the prior art employing a tube of fine diameter as a passage.

Although in the first preferred embodiment, the passage forming member 15 is made of a resin material, e.g., plastic, it may be formed by machining other material, e.g., glass or metals. The molding method is not limited to injection mold and various well-known molding methods can be employed. This is true for the following preferred embodiments as well.

Although in the first preferred embodiment, the channel 151 is provided in the surface of the passage forming member 15 of a columnar shape, the passage forming member 15 may have an arbitrary sectional form. For example, solid or hollow columnar ones having columnar, multi-prismatic or cylindrical shape can be adopted, provided only that the surface of the passage forming member 15 is brought into close contact with the inner surface of the casing 13 (the housing part 14) to introduce a liquid toward the outlet part 12 along the channel 151. This is true for the following preferred embodiments as well.

Although in the first preferred embodiment, the channel 151 is spirally provided in the surface of the passage forming member 15, the channel 151 is merely required to be formed windingly such as to have a length sufficiently longer than the whole length L of the passage forming member 15, and it may be wound in random fashion. Accordingly, the liquid discharge regulator may be arranged as shown in FIG. 3 or 4.

Figure 3:
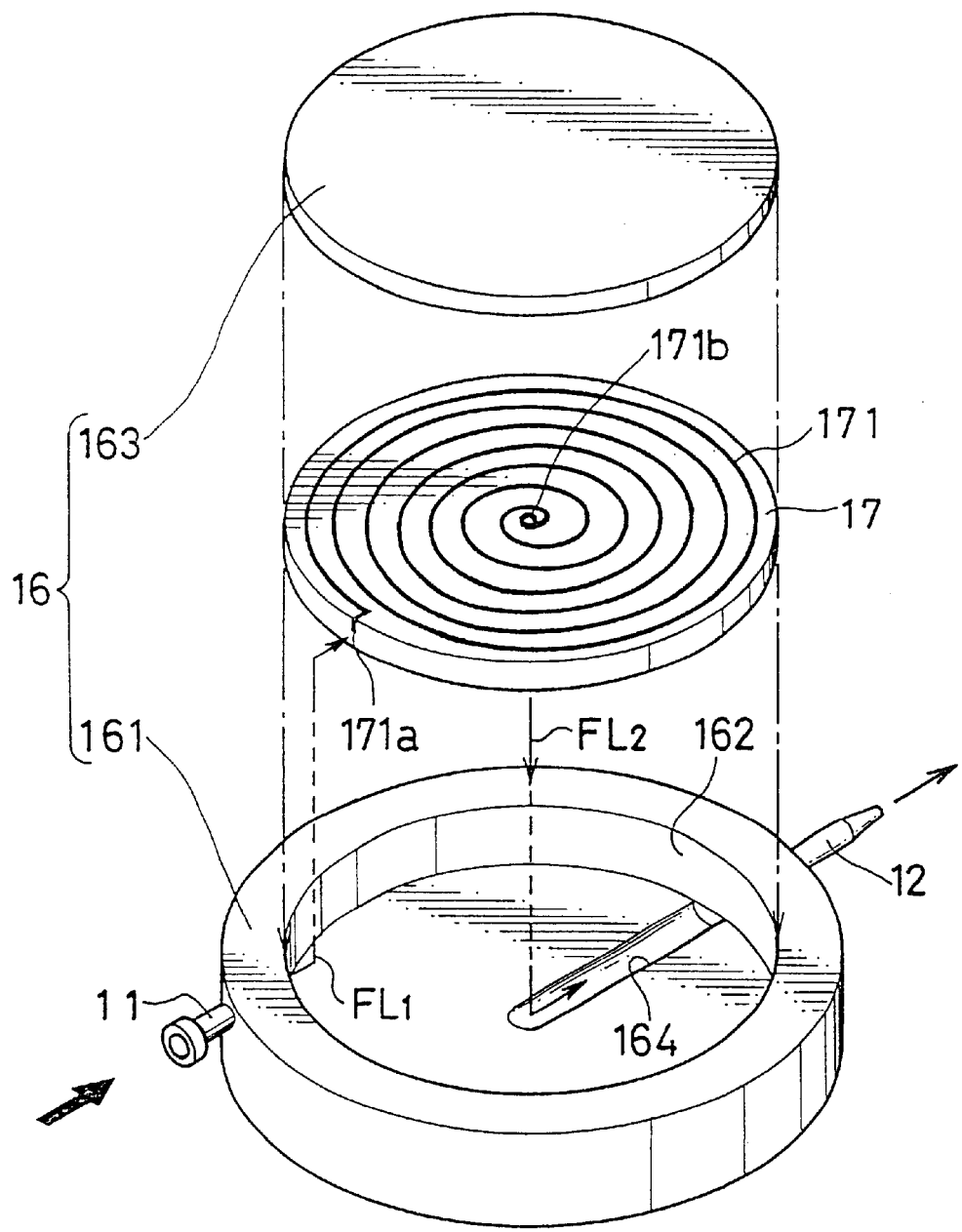
FIG. 3 is a disassembled perspective view of a modification of the discharge regulator of FIGS. 1A to 1C.

FIG. 3 is a disassembled perspective view showing a modification of the discharge regulator of FIGS. 1A to 1C. In a discharge regulator 1, an inlet part 11 and an outlet part 12 project in directly opposite direction from the side surface of a disk-like base part 161. A circular recess 162 is disposed centrally of the upper surface of the base part 161, and the recess 162 is arranged to allow for the engagement of a disk-like passage forming member 17. A cover part 163 is press-inserted into the recess 162 to cover the discharge forming member 17 from its top surface, so that the top surface of the discharge forming member 17 is brought into close contact with the surface of the cover part 163. Thus, in this embodiment, a casing 16 includes the base part 161 and the cover part 163, and a housing space for housing the discharge forming member 17 is formed by the base part 161 and the cover pat 163. That is, the recess 162 functions as a housing part, in this embodiment.

A spiral channel 171 is formed in the top surface of the discharge forming member 17. With the member 17 housed in the recess (housing part) 162, a peripheral end 171a of the recess 171 is opposed to the inlet part 11 and, as shown by arrow FL1 in FIG. 3, when a liquid runs to the discharge forming member 17 via the inlet part 11, the liquid is introduced to almost centrally of the surface of the discharge forming member 17 along the channel 171. An end 171b disposed centrally of the channel 171 is in communication with a communication channel 164 disposed in the top surface of the base part 161 via a through-hole (not shown) passing through vertically of the discharge forming member 17. As shown by arrow FL2 in FIG. 3, the liquid that has reached the end 171b along the channel 171 serving as a passage, runs in the communication channel 164 via the through-hole, goes to the outlet part 12 along the communication channel 164, and then flows out through the outlet part 12.

Figure 4:
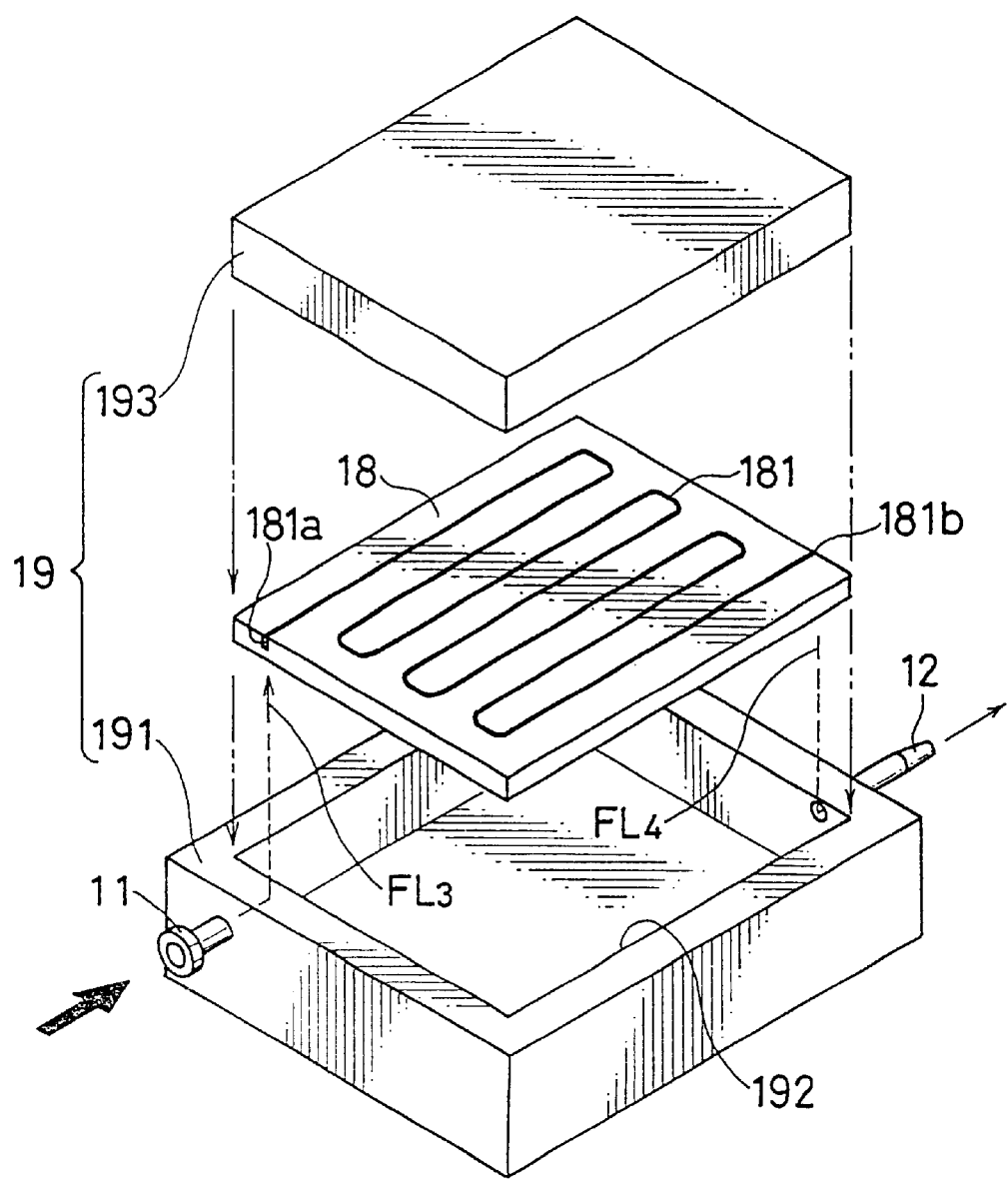
FIG. 4 is a disassembled perspective view of another modification of the discharge regulator of FIGS. 1A to 1C.

FIG. 4 is a disassembled perspective view showing another modification of the discharge regulator of FIGS. 1A to 1C. This discharge regulator distinctly differs from the previous one in that a passage forming member 18 includes a rectangular flat plate and its top surface is formed with a snaky (winding) channel 181, and that both ends 181a and 181b of the channel 181 are directly connected to an inlet part 11 and an outlet part 12, respectively, which project from the side surface of a base part 191 constituting a casing 19. Other constructions are substantially the same. Therefore, as shown by arrow FL3 in FIG. 4, when a liquid runs in the discharge forming member 18 via the inlet part 11, the liquid reaches the end 181b along the channel 181 serving as a passage and, as shown by arrow FL4 in FIG. 4, reaches the outlet part 12 and then flows out through the outlet part 12. In FIG. 4, reference numerals 192 and 193 designate components corresponding to the recess 162 and the cover part 163 of the device of FIG. 3.

As stated above, the liquid discharge regulators according to the above modifications employ, as a liquid passage, the channels 171 and 181 sufficiently longer than the whole length of the passage forming members 17 and 18, which are formed in the surface of the members 17 and 18, respectively, as does the case with the device of FIGS. 1A to 1C. This enables the invention to provide a compact device at low a cost.

B. Second Preferred Embodiment

Figure 6A:
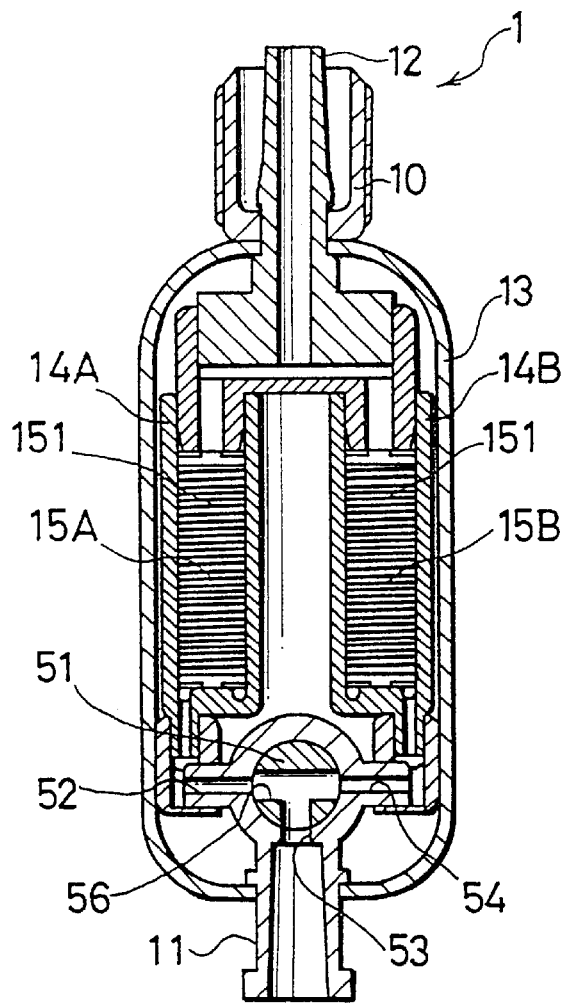
FIGS. 6A to 6C are cross sections of the above discharge regulator.
Figure 6B:
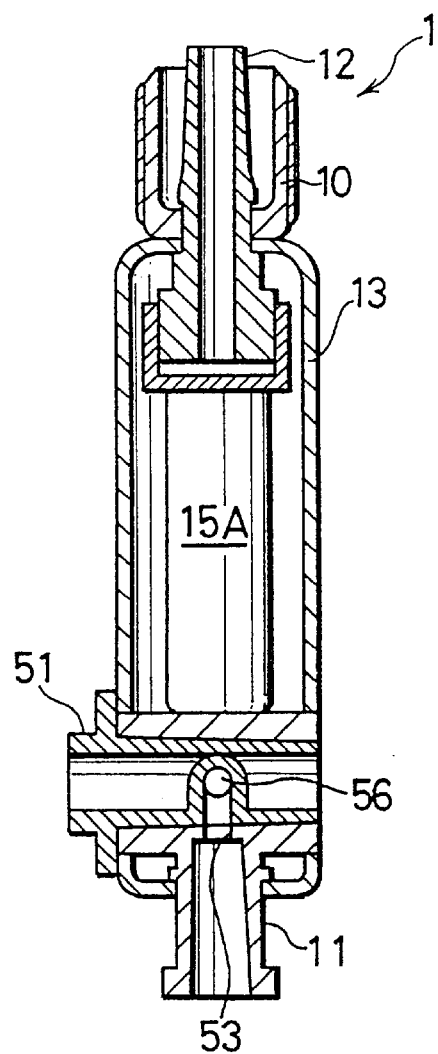
Figure 6C:
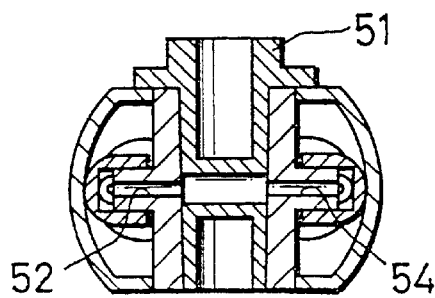

FIGS. 5A and 5B are diagrams of a liquid discharge regulator according to a second preferred embodiment of the invention. FIGS. 6A to 6C are cross sections of the discharge regulator of FIGS. 5A and 5B. FIG. 6A is a cross section taken along the line 6A—6A of FIG. 5B; FIG. 6B is a cross section taken along the line 6B—6B of FIG. 5A; and FIG. 6C is a cross section taken along the line 6C—6C of FIG. 5A.

Referring to FIGS. 6A to 6C, in a discharge regulator 1, two housing parts 14A and 14B are provided in a casing 13 to define two independent cylindrical housing spaces. Discharge forming members 15A and 15B are housed in the housing members 14A and 14B, respectively. When comparing the discharge forming member 15A with 15B, it is common that channels 151 of the same sectional form are formed in their respective surfaces and the surfaces are rendered into close contact with the inner surface of the housing members 14A and 14B. Thereby, the channel 151 functions as a liquid passage, similar to the first preferred embodiment. On the other hand, the channel 151 is spirally formed in a relatively wider pitch in the surface of the passage forming member 15A, whereas the channel 151 is spirally formed in a relatively narrower pitch in the surface of the passage forming member 15B. As a result, in this embodiment, the pipe loss of the passage forming member 15A is smaller than that of the member 15B, and the discharge RA of liquid flowing through a passage A on the side of the passage forming member 15A (see FIG. 7) is different from the discharge RB of liquid flowing through a passage B on the side of the passage forming member 15B (see FIG. 7). Other structural features of the passage forming members 15A and 15B are the same as those of the passage forming member 15 in the first preferred embodiment.

Figures 7, 8:
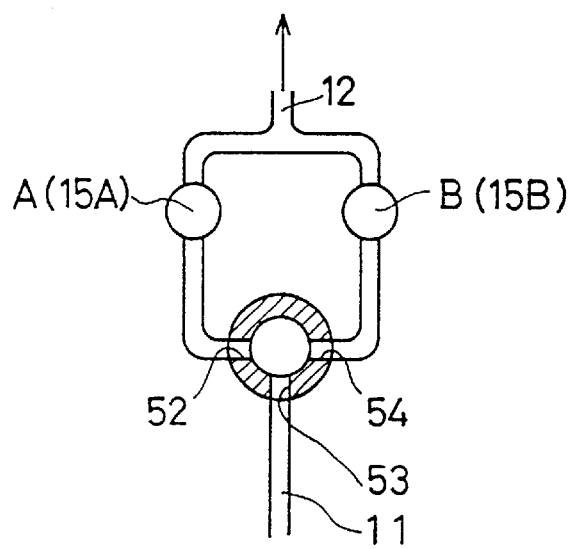
FIG. 7 is a schematic view illustrating the relationship between a passage branching part and a passage in the above discharge regulator.
FIG. 8 is a diagram illustrating the relationship between the rotating amount of a control stopper and the discharge.

As shown in FIG. 6A, the housing members 14A and 14B are in communication with the inlet part 11 via a passage branching part 5 on the side of the inlet part 11, while they are in directly communication with the outlet part 12 on the side of the outlet part 12. A control stopper 51 is rotatably engaged in the interior of the passage branching part 5. FIGS. 7 and 8 illustrate schematically a passage branching part 5 and a control stopper 51. The passage branching part 5 is formed with three valve holes 52, 53 and 54 which have an open angle of 90° in three directions, respectively, on a plane orthogonal to the axis of rotation of the control stopper 51. The valve hole 53 is connected to the inlet part 11 and the valve holes 52 and 54 provided in the sides are connected to the housing members 14A and 14B, respectively. A T-shaped communication path 56 is formed in the control stopper 51, and a switching valve part is constructed by allowing each opening of the communication path 56 to match or mismatch the respective valve holes 52, 53 and 54.

As shown in FIGS. 5A, 5B and FIGS. 6A to 6C, one end of the control stopper 51 passes through the casing 13 for exposure to the outside, and the exposed part is defined as an operation input part 57. The operation input part 57 is shaped to a hexagon nut and free to rotate by an engagement with an operation tool in the form of a closed wrench (not shown). Disposed in the periphery of the operation input part 57 is an indicator 58 which facilitates an understanding of the direction of the control stopper 51 (the communication path 56). Disposed in the casing 13 is a scale which indicates the selection situation (the flow rate) of the passages A and B in response to the indicator 58.

Referring now to FIG. 8, a description is now given on the relationship between the rotating amount of the control stopper 51 and the discharge of liquid flowing through the outlet part 12. As to "rotation angle" in FIG. 8, assuming it is "0°" when the control stopper 51 is not operated, the respective rotation angles are indicated when the control stopper 51 is rotated in a clockwise direction as seen in FIGS. 6A to 6C, from the connecting status at 0°. The connecting status at the respective rotation angles are schematically shown in the column of "connected state," and the respective discharges of liquid through the outlet part 12 are indicated in the column of "discharge."

When the control stopper 51 is not operated, the valve hole 53 on the side of the inlet part 11 has no communication with the valve hole 52 or 54, and thus both passages A and B are closed.

When the control stopper 51 is rotated 90° clockwise from the state indicated uppermost of the "connected state" column, only the valve holes 53 and 54 are brought into communication. Thereby the passage B alone is selected for fluid communication. As a result, a liquid is discharged from the outlet part 12 at a discharge RB according to the pipe loss of the passage B.

When the control stopper 51 is rotated 180°, the valve holes 52, 53 and 54 are all brought into communication, thereby both passages A and B are selected for fluid communication. As a result, a liquid is discharged from the outlet part 12 at the total discharges (RA+RB) according to the respective pipe losses of the passages A and B.

When the control stopper 51 is rotated 270°, only the valve holes 52 and 53 are brought into communication. Thereby the passage A alone is selected for fluid communication. As a result, a liquid is discharged from the outlet part 12 at a discharge RA according to the pipe loss of the passage A.

As stated above, in the second preferred embodiment, the two housing parts 14A and 14B are disposed in the casing 13 and the passage forming members 15A and 15B having different pipe losses are housed in their respective housing parts 14A and 14B to obtain liquid passages A and B which are arranged such that they are selectively switched by operation of the control stopper 51. This permits a three-stage regulation of the charge of liquid through the outlet part 12. That is, the passage branching part 5 and the control stopper 51 function as passage switching means.

Since the spiral channel 151 in the surfaces of the passage forming members 15A and 15B is arranged to function as liquid passages A and B, the same effect as the first preferred embodiment is obtained in addition to the above-mentioned effects.

Although in the second preferred embodiment, the passage forming members 15A and 15B are provided with the channels 151 having the same shape and different lengths such that the passages A and B differ from each other in pipe loss, the channels 151 may have the same length and different sectional areas or may have different sectional areas and lengths such that the passages A and B have different pipe losses.

Although in the second preferred embodiment, the two passages A and B are formed and switching of discharge is controlled by rotating the control stopper 51 of the passage branching part 5 serving as passage switching means, three or more passages may be provided to switch the discharge. Specifically, three or more housing parts are disposed in the casing 13 and passage forming members having different pipe losses are housed in the respective housing parts, such that selective switching of passage is effected by passage switching means.

Although in the second preferred embodiment, the passage branching part 5 serving as passage switching means is provided on the side of the inlet part 11, it may be positioned anywhere between the inlet part 11 and the outlet part 12, for example, between the outlet part 12 and the housing part 14A or 14B.

Although in the second preferred embodiment, a spiral channel is provided as a passage forming member in a cylindrical member, as in the case with the first preferred embodiment, any modifications described in the first preferred embodiment may be made in shape, material, and winding form.

C. Third Preferred Embodiment

FIGS. 9A and 9B are diagrams showing a liquid discharge regulator according to a third preferred embodiment of the invention. This discharge regulator is distinctly different from that of the second preferred embodiment in that a bypass passage C is substituted for the passage B which is formed by disposing the passage forming member 15B in the housing part 14B, and that a bypass passage switching part 6 for switching the bypass passage is substituted for the passage branching part. Other basic constitutions are the same. Therefore, a description is made in detail on the differences. Similar reference numerals have been used to denote similar parts and therefore its description is omitted.

In a discharge regulator 1, a bypass pipe 7 which includes serially-connected two pipes 71 and 72 parallel to a housing part 14A, is disposed between an inlet part 11 and an outlet part 12 to define a bypass passage C. The pipes 71 and 72 may have an arbitrary sectional form which is much greater than that of a channel 151. This enables the invention to provide liquid communication with the outlet part 12 via the bypass passage C in a sufficiently larger amount than the flow rate of a passage A formed by a passage forming member 15A.

A bypass passage switching part 6 for switching the bypass passage C is provided in the junction between the pipes 71 and 72. As shown in FIG. 9B, an opening 61 is disposed in the junction between the pipes 71 and 72, and a liquid flows from the pipe 71 to the pipe 72 via the opening 61. An operating rod 62 is slidably mounted in the opening 61. A distal end 621 of the operating rod 62 is located in a casing 13 while a rear end 622 projects outwardly of the casing 13. When the rear end 622 is pushed against the side of the casing 13, the distal end 621 of the operating rod 62 closes the opening 61 to close the bypass passage C, as shown in FIG. 9B. When the rear end 622 is drawn out of the casing 13, the distal end 621 is withdrawn from the opening 61 to open the bypass passage C. Thus, the bypass passage switching part 6 is composed of the opening 61 and operating rod 62 in this embodiment.

In the liquid discharge regulator 1 so constructed, when the operator pushes the operating rod 62 against the casing 13 to close the bypass passage C, only the passage A which is constructed in the same manner as in the first preferred embodiment is brought into fluid communication, and a liquid is discharged from the outlet part 12 at the discharge corresponding to the pipe loss of the passage A. This produces the same effect as the first preferred embodiment.

If it is desired to sharply increase the discharge of liquid in response to the change of patient's condition and the efficacy of chemical liquid, the discharge regulator 1 of this embodiment is suitably applicable to such a case. That is, when the operator draws the operating rod 62 from the casing 13 to open the bypass passage C, both passages A and C are brought into fluid communication. Then it is possible to discharge liquid through the outlet part 12 in a sufficiently larger amount than the flow rate of the passage A because the pipes 71 and 72 have the cross sections considerably greater than that of the channel 151 as stated earlier.

Although in the third preferred embodiment, the bypass passage C is switched by closing/opening the opening 61 with the operating rod 62, the bypass passage switching part 6 is not limited to this arrangement. For example, it may be constructed by the control stopper as used in the second preferred embodiment.

Although in the third preferred embodiment, the bypass passage C is added to a discharge regulator of the type in which only the passage A is provided for fine adjustment of liquid discharge (the first preferred embodiment), the present invention is applicable to discharge regulators of the type which have a plurality of passages as in the second preferred embodiment.

D. Fourth Preferred Embodiment

Figure 11:
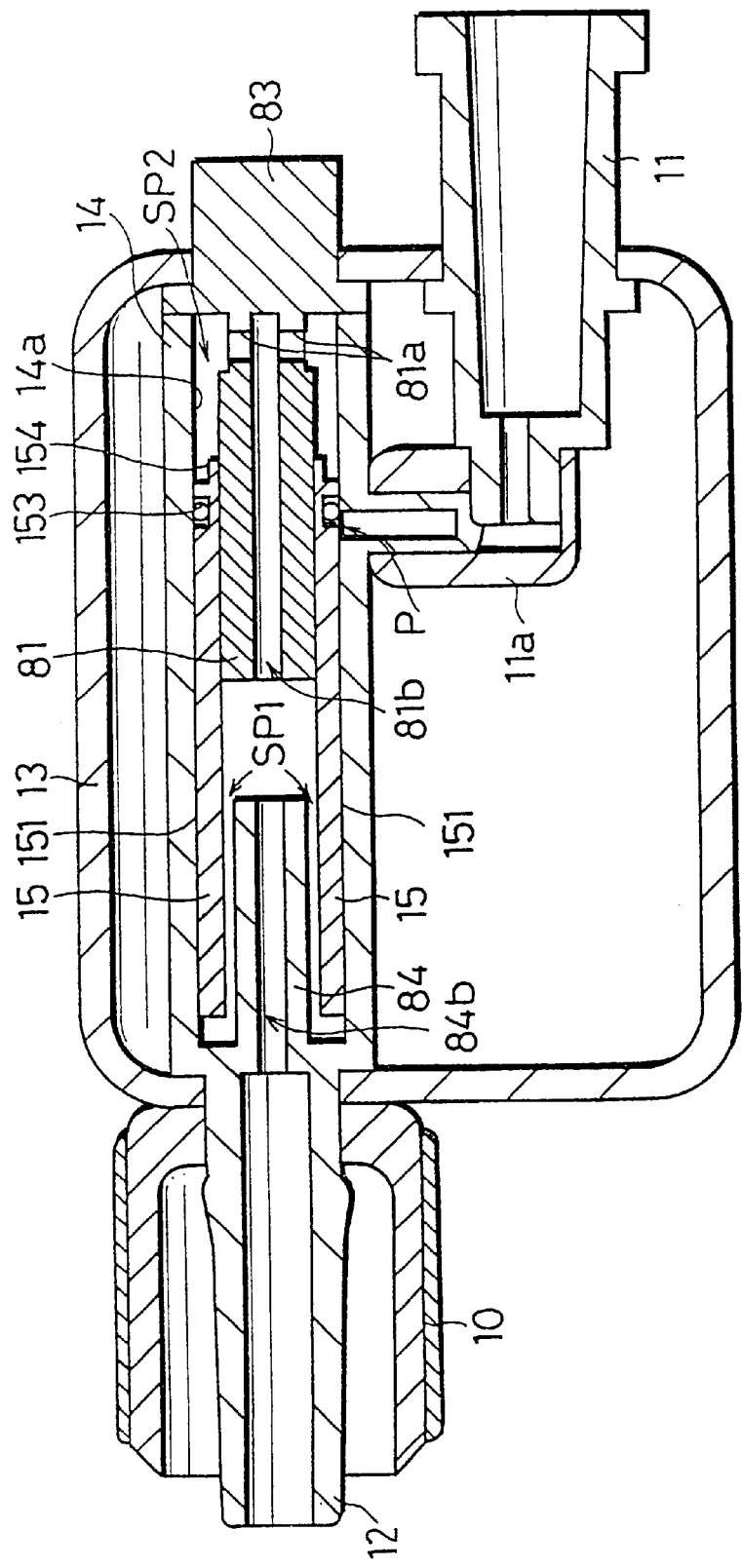
FIG. 11 is a cross section of the discharge regulator taken along the line 11—11 of FIG. 10B.
Figure 12:
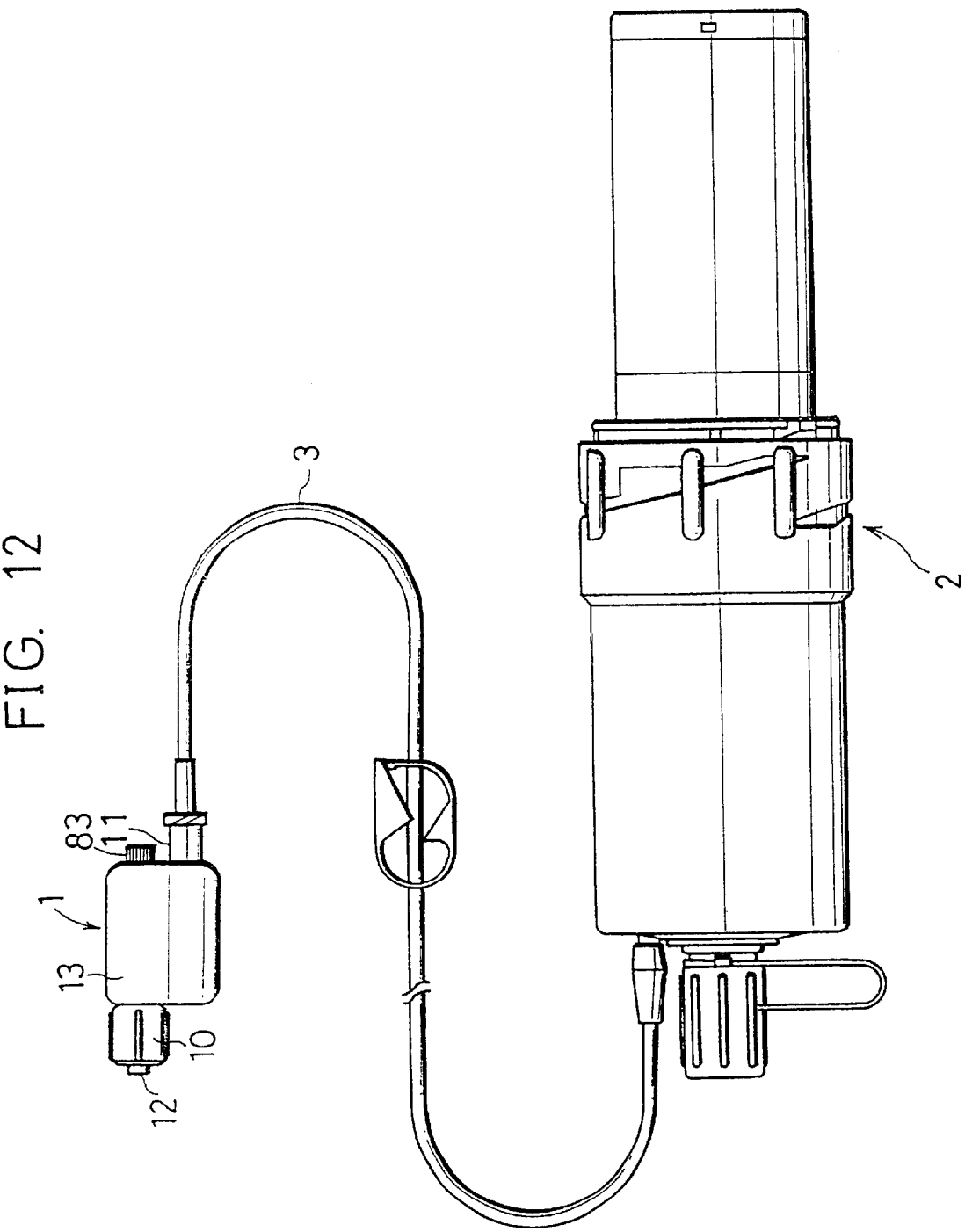
FIG. 12 is a diagram showing a situation where the discharge regulator of FIGS. 10A and 10B is put into service.

FIGS. 10A and 10B are diagrams showing a liquid discharge regulator according to a fourth preferred embodiment of the invention. FIG. 11 is a cross section taken along the line 11—11 of the FIG. 10B. FIG. 12 is a diagram illustrating a situation where the discharge regulator of FIGS. 10A and 10B is placed in service.

Referring to FIG. 12, a discharge regulator 1 is used in combination with a liquid feeder 2. That is, a tube 3 extending from the liquid feeder is connected to an inlet part 11 of the discharge regulator 1, and another tube (not shown)to be connected to the body is connected to an outlet part 12. It is therefore possible to inject a liquid in portions into the body over a long period of time. Reference numeral 10 designates a lock part, by which the tube connected to the body (not shown) attached to the outlet part 12 is fastened and locked to the outlet part 12.

Referring to FIG. 11, in the discharge regulator 1, the inlet part and the outlet part 12 are attached to the side surface of a casing 13 in directly opposite direction. A housing part 14 is disposed in the casing 13 such as to lie in line with the outlet part 12. A housing space 14a is defined by the housing part 14 and it is arranged such that the liquid supplied to the inlet part 11 runs into the housing space 14a from the side surface of the housing part 14 by a connecting member 11a. From one end side of the casing 13 (the right side as viewed in FIG. 11), a passage forming member 15 is engaged to the housing space 14a of the housing part 14.

Figure 13:
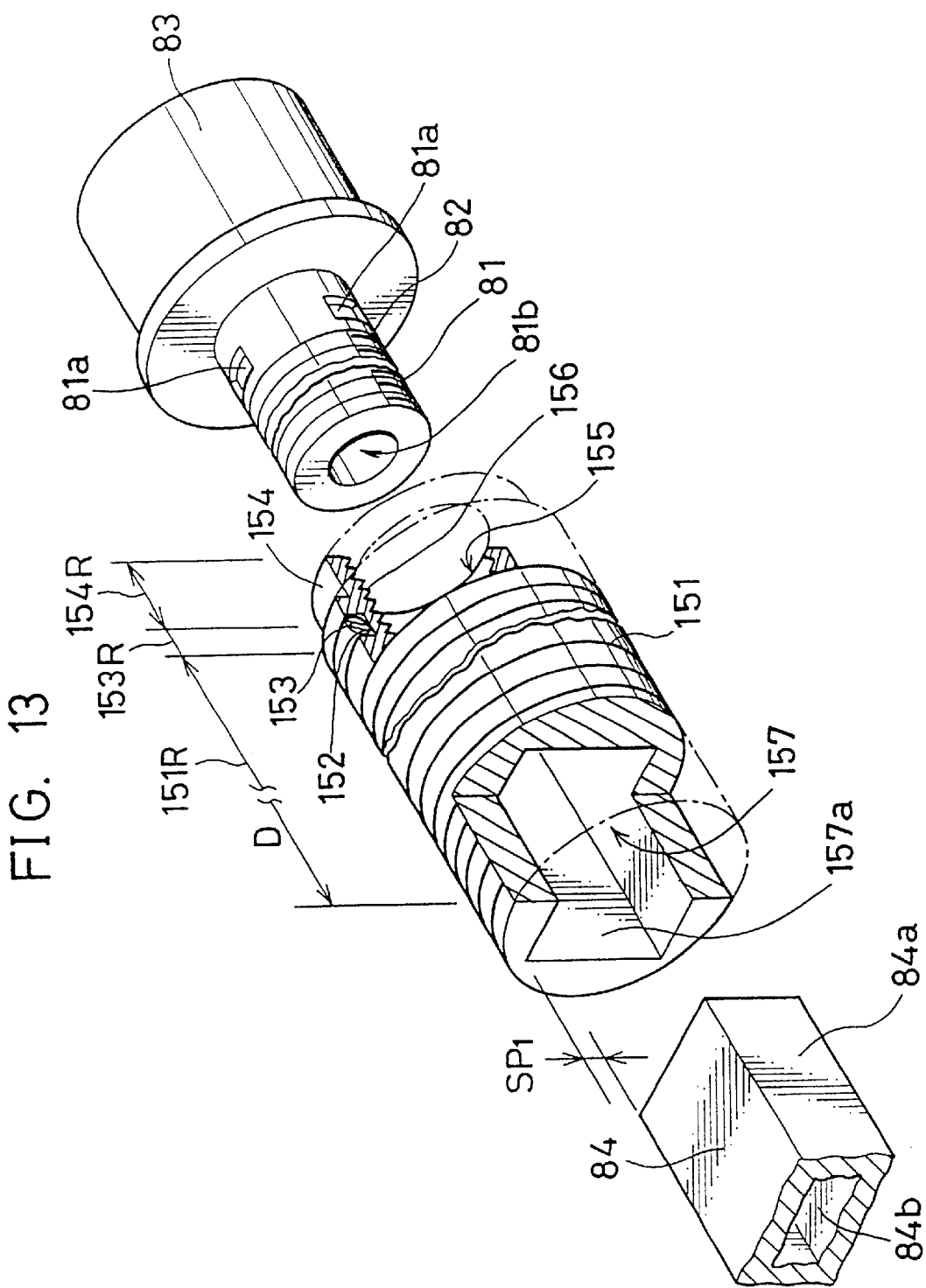
FIG. 13 is a perspective view, partially broken away, of a passage forming member.

FIG. 13 is a perspective view, partially broken away, of a passage forming member 15. The member 15 is made of a resin material, e.g., plastic, in a hollow cylindrical shape, and its outside diameter is approximately the same as the inside diameter of the housing part 14. The discharge forming member 15 is free to move in the longitudinal direction of the housing space 14a while being brought into close contact with the inner surface of the housing part 14. A channel 151 is spirally formed in the surface of the passage forming member 15, and it has a sectional form of rectangle, triangle or semicircle, for a given distance D from the other end (the lower left-hand as seen in FIG. 13). As a result, the liquid that has reached the housing space 14a from the side surface of the housing part 14 via the connecting member 11a can be introduced along the spiral channel 151. Thereby, the channel 151 functions as a liquid passage.

A rectangular channel 152 is provided on one side (the upper right-hand as seen in FIG. 13) of the channel 151 and an O ring 153 is embedded within the rectangular channel 152, so as to regulate a liquid which flows via the O ring 153 from one to the other side or in reverse direction, along the surface of the passage forming member 15. A region 153R corresponding to the O ring 153 functions as a regulation region.

In a peripheral region 154R extending from one end to the other end of the O ring 153 on the surface of the passage forming member 15, there is a bypass part 154 whose outside diameter is smaller than that of the region 151R where the channel 151 is formed. The bypass part 154 functions to introduce the liquid that has reached via the input part 11 into a bypass passage, as is described below.

One side of the hollow region of the passage forming member 15 is a cylindrical hollow region 155 and the other side thereof is a prismatic hollow region 157. An internal thread 156 is screwed into the internal peripheral surface of the hollow region 155.

A hollow cylindrical member 81 is arranged such as to fit into the cylindrical hollow region 155. An external thread 82 corresponding to the internal thread 156 is screwed into the outer peripheral surface of the cylindrical member 81 for engagement with the internal thread 156, as shown in FIG. 11. A control knob 83 is fixedly attached to one end of the cylindrical member 81 (the end on the right-hand as viewed in FIG. 11) and the control knob 83 is rotatable relative to the casing 13 and the housing part 14, with its distal end projecting from the casing 13 (see FIG. 11). In FIGS. 11 and 13, reference numeral 81a designates through-holes to allow communication between the peripheral part of the cylindrical member 81 and the hollow region 81b. Four through-holes 81a are disposed equidistantly around the peripheral surface of the cylindrical member 81.

Disposed in the prismatic hollow region 157 is a hollow prismatic member 84 which projects from the other end of the housing part 14 to the side of the passage forming member 15. The widthwise inside diameter of the prismatic member 84 is the same or slightly smaller than the inside diameter of the hollow region 157 such that a side part 84a of the prismatic member 84 (see FIG. 13) is brought into contact with the hollow region 157. On the other hand, the heightwise diameter of the prismatic member 84 is smaller than the inside diameter of the hollow region 157, thereby producing a heightwise space SP1.

As stated above, in this embodiment it is arranged such that one end of the passage forming member 15 is subjected to the torque of the control knob 83 and the other is brought into contact with the side part 84a of the prismatic member 84. Therefore, the passage forming member 15 is guided by the prismatic member 84 to reciprocate within the housing part 14 according to the rotating amount of the control knob 83. By operating the control knob 83, position P of the channel 151 opposite the inlet part 11 via the connecting member 11a is changed to correct the length of the channel 151 from the position P to the outlet part 12; the inlet part 11 and the O ring 153 (the regulation region 153R) are oppositely disposed via the connecting member 11a to regulate the flow of liquid into the side of the outlet part 12;

or the inlet part 11 is oppositely disposed with the bypass part 154 having a smaller outside diameter than that of the region 151R formed with the channel 151.

Figure 14A:
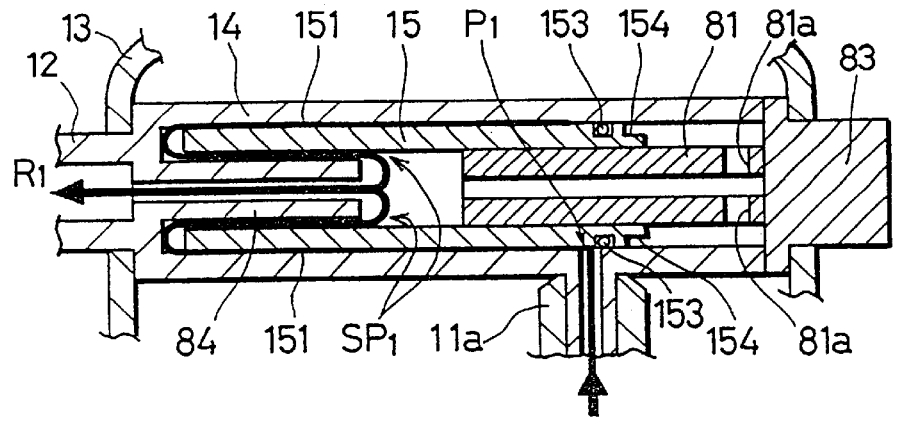
FIGS. 14A to 14C are diagrams showing discharge regulating operation in the discharge regulator of FIGS. 10A and 10B.
Figure 14B:
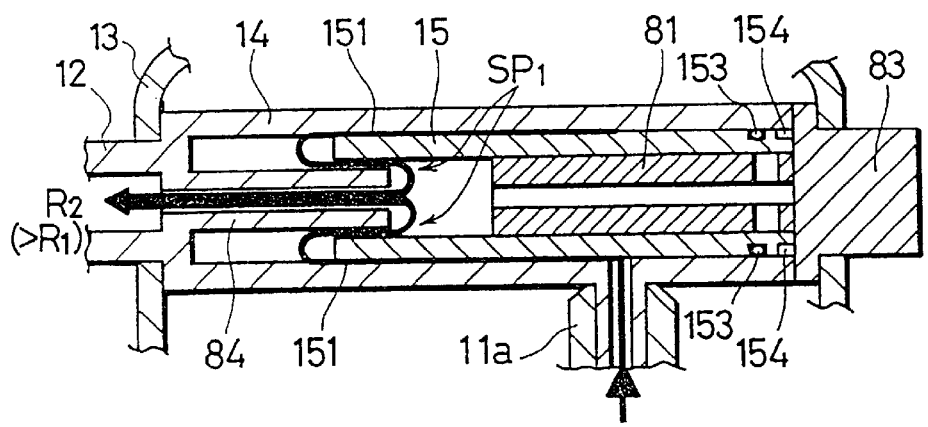
Figure 14C:
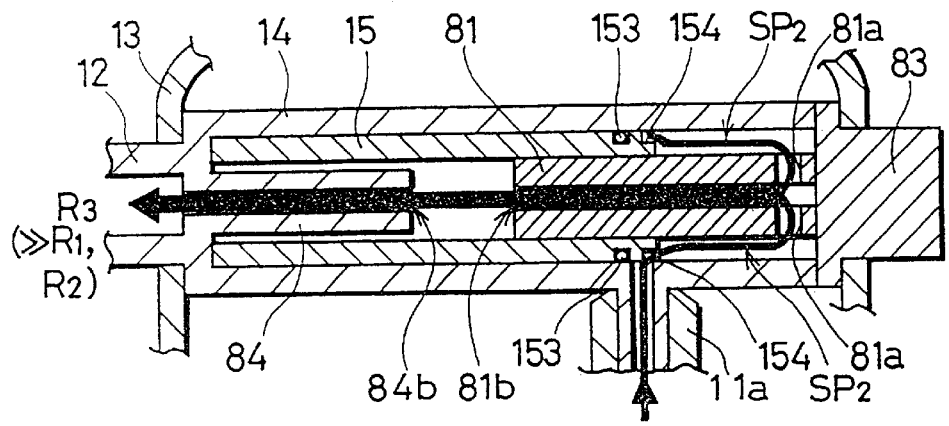

Referring to FIGS. 14A to 14C, description will now be made on liquid discharge changes when the passage forming member 15 is set at various positions by the control knob 83. In the figures, solid arrows designate the flow of liquid which has been forced to the housing space 14a via the inlet part 11 and the connecting member 11a.

As shown in FIG. 14A, when the control knob 83 is operated such that position P1 closely adjacent an O ring 153 in a region 151R formed with a channel 151 is located opposite the inlet part 11 via the connecting part 11a, the liquid forced to the housing part 14 via the inlet part 11 and the connecting member 11a runs to the side of the outlet part 12 along the channel 151, passes the space SP1 between the hollow region 157 of the passage forming member 15 and the prismatic member 84, goes through the hollow region 84b of the prismatic member 84, and reaches the outlet part 12. At this time, since the liquid passes through the almost entire length of the channel 151, the pipe loss of the passage formed by the channel 151 is relatively high and thus the discharge R1 of the liquid flowing through the outlet part 12 becomes relatively low.

As the control knob 83 is operated to move the passage forming member 15 to the side of the control knob 83, the position opposite the inlet part 11 via the connecting member 11a is gradually moved to the side of the outlet part 12. Thus, in response to the rotation of the control knob 83, the length of the channel 151 from the above-mentioned position to the outlet part 12 becomes gradually shorter and the pipe loss also becomes smaller. As a result, the liquid is introduced into the outlet part 12 through the same path as shown in FIG. 14A, and the discharge of the liquid flowing through the outlet part 12 is gradually increased. Then, as shown in FIG. 14B, when one end of the passage forming member 15 is engaged in the control knob 83, the length of the channel 151 from position P2 opposite the inlet part 11 via the connecting member 11a to the outlet part 12 becomes the shortest and the pipe loss becomes the smallest, so that the discharge of the liquid flowing through the outlet pat 12 results in R2(>R1).

Subsequently, when the control knob 83 is rotated in reverse direction to move the passage forming member 15 away from the control knob 83, in just the reverse fashion to the above, the length of the channel 151 from the position opposite the inlet part 11 via the connecting member 11a to the outlet part 12 becomes gradually longer and the pipe loss also becomes gradually larger, thereby reducing the discharge of the liquid flowing through the outlet part 12. Then, if returned to the state shown in FIG. 14A, the discharge of the liquid flowing through the outlet part 12 results in the minimum value R1. When the control knob 83 is further rotated in the same direction, the inlet part 11 is located opposite the O ring 153 (the regulation region 153R) via the connecting member 11a, so that the inlet part 11 is substantially closed by the O ring 153. As a result, the flow of liquid toward the inlet part 12 is regulated and the discharge from the outlet part 12 falls to zero.

In this regulated state, when the control knob 83 is further rotated in the same direction, the inlet part 11 is located opposite the bypass part 154 via the connecting member 11a, and the liquid is introduced into the outlet part 12 via a bypass passage which comprises the following in the order named: the space SP2 between the housing part 14 and the cylindrical member 81; the through-hole 81a; the hollow region 81b of the cylindrical member 81; the housing space 14a; and the hollow region 84b of the prismatic member 84. This bypass passage has a sectional area much greater than that of the channel 151 throughout its whole length, and the liquid is introduced into the outlet part 12 via the bypass passage in a sufficiently greater amount (discharge R3>>R1, R2) than the flow rate of the passage formed by the passage forming member 15.

As stated above, in the liquid discharge regulator of this embodiment, the control knob 83 is operated to change the length of the channel 151 from the position of the channel 151 (e.g., the position P, P1, or P2) opposite the inlet part 11 via the connecting member 11a to the side of the outlet part 12, and the pipe loss of the channel 151 located at that position is continuously corrected, so that the discharge of liquid flowing through the outlet part 12 is continuously regulated. This permits a fine regulation of liquid discharge in response to the change of patient's condition and the efficacy of chemical liquids.

This also leads to a compact device because unlike the prior art, it is unnecessary to form in advance a plurality of passages of different pipe losses by disposing a plurality of tubes of fine diameter.

If desired to sharply increase a liquid discharge in response to the change of patient s condition and the efficacy of chemical liquids, a desired discharge is obtained by operating the control knob 83 such that the bypass part 154 is located opposite the inlet part 11 via the connecting member 11a.

In the liquid discharge regulator 1 of this embodiment, the channel 151 formed spirally in the surface of the passage forming member 15 is used as a liquid passage, resulting in the same effect as in the first to third preferred embodiments.

Although in the fourth preferred embodiment the passage forming member 15 is moved by the control knob 83, the housing part 14 may be moved instead of the passage forming member 15, or both may be moved to change the position P of the channel 151 opposite the inlet part 11 via the connecting member 11a. That is, with the arrangement to permit the relative movement of the passage forming member 15 with respect to the inlet part 11, the discharge of the liquid flowing through the outlet part 12 is regulatable over a wide range by changing the length of the channel 151 from the position P opposite the inlet part 11 to the outlet part 12, or by locating the inlet part 11 opposite the bypass part 154.

Although in the fourth preferred embodiment the passage forming member 15 is moved relative to the inlet part 11, it may be moved relative to the outlet part 12 such as to change the length of the channel 151 from the position opposite the outlet part 12 to the outlet part 12. With this arrangement, the same effect as in the foregoing embodiments is obtained.

E. Others

As shown in FIG. 1C, in the above discharge regulator 1, it is arranged such that the diameter of the passage forming member 15, 15A, 15B is reduced gradually as it advances along the channel 151 on the side of the inlet part 11. This produces the following effect. Specifically, some of liquids which are subjected to discharge regulation (e.g., physiological salt solution) is partially crystallized at discontinuous portions due to a sharp reduction in passage diameter. If such a crystallization occurs within the passage, its crystalline might clog the passage. In this invention, however, liquid crystallization is reliably prohibited to prevent a clogging of the passage, by virtue of gradual reduction in passage diameter as stated earlier.

Liquid Feeders

Figure 15:
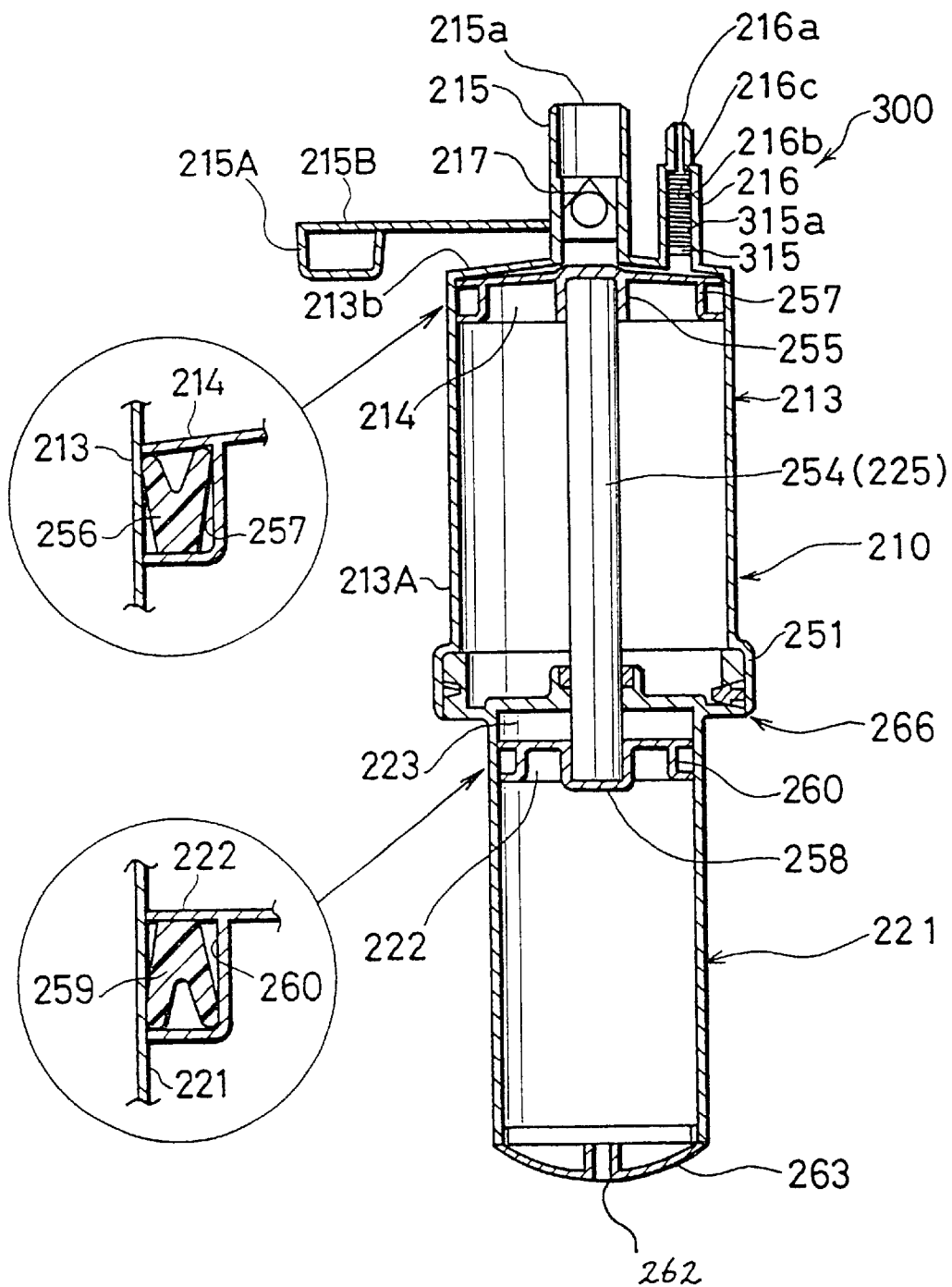
FIG. 15 is a cross section of one preferred embodiment of a liquid feeder according to the invention.

FIG. 15 is a cross section showing one preferred embodiment of a liquid feeder according to the invention. This liquid feeder includes a casing (a device body) 213 capable of storing a liquid therein; a cylinder 221 with which the liquid stored inside of the casing 213 is forced to an outlet part 216 disposed at the distal end side (the upper side as viewed in FIG. 15) of the casing 213; and a discharge regulation section 300, disposed in the outlet part 216 of the casing 213, for introducing the liquid fed by the cylinder 221 into an outlet 216a and regulating the discharge of the liquid flowing through the outlet 216a.

Figure 16:
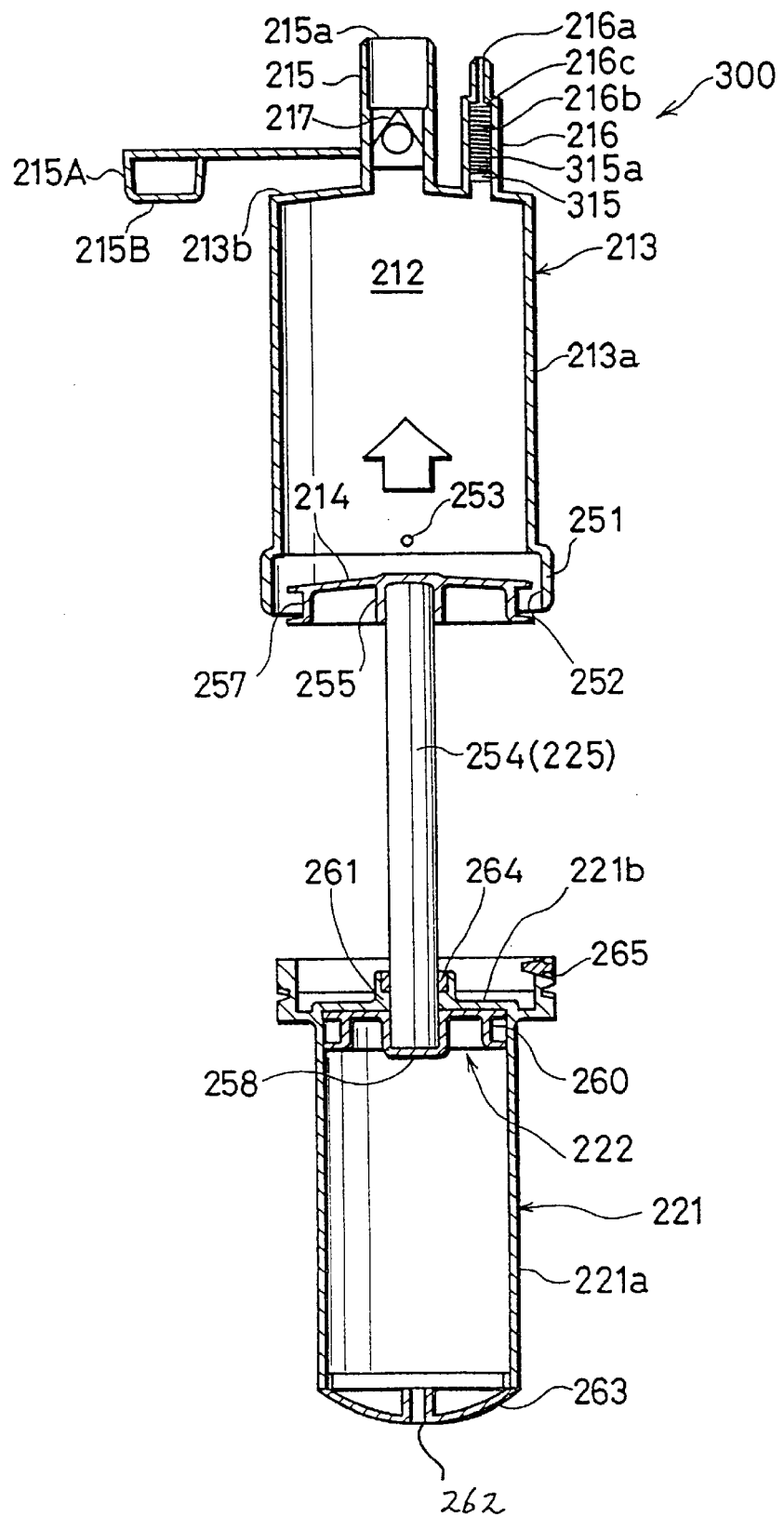
FIG. 16 is a cross section illustrating a state before a cylinder is attached to a casing.

FIG. 16 a cross section illustrating a state before a cylinder is attached to a casing. A casing 213 is shaped into a cylinder, the distal end of which (the upper end as seen in FIGS. 15 and 16) is closed by a bottom wall 213b, and the rear end (the lower end as seen in FIGS. 15 and 16) is opened. An injection part 215 and an outlet part 216 extend upwardly from the bottom wall 213b. The injection part 215 has an inlet 215a for injecting a liquid into the casing 213, and a check valve (a valve gear) 217 is disposed therein. A cap 215A which is removable from the distal end of the inlet 215a is attached to the side wall of the injection part 215 via a connecting string 215B.

The outlet part 216 has an outlet 216a for discharging a liquid externally of the feeder, and a discharge regulation section 300 is disposed in the interior of the outlet part 216. The discharge regulation section 300 will be described later in detail.

As to the casing 213 and a cylinder 221 as described later, if at least the casing 213 is made of a transparent or translucent synthetic resin, the casing 213 may carry a scale for accurate measurement of the liquid to be filled and stored in a storage chamber 212.

The other end opening of a side wall 213a of the casing 213 is formed with a slightly outwardly flared part 251, an internal thread 252 is formed in the inner surface of the flared part 251, and a small hole 253 connecting the interior of the casing 213 with atmosphere is formed in the vicinity of the flared part 251. The small hole 253 places the space of the rear surface side (the lower side as seen in FIGS. 15 and 16) of a movable body 214 in the casing 213 into communication with the atmosphere, in order to allow for axial movement of the movable body 214. The small hole 253A is closed by a filter (not shown) which permits communication of atmosphere but blocks intrusion of bacteria. Therefore, when the liquid feeder is continuously used, for example, when a liquid is injected into the body while being fed through the inlet 215a, the above filter blocks intrusion of bacteria into the liquid, thereby avoiding human infection.

In order to form the storage chamber 212 for storing the liquid running through the inlet 215a on one end side (the upper side as seen in FIGS. 15 and 16) in the casing 213, the movable body 214 is inserted in the casing 213 such that it is in fluid-tight and movable in an axial direction. As shown in FIG. 15, similar to the bottom wall 213b of the casing 213, the movable body 214 is shaped into a disk whose central part has a slightly expanded tapered surface. A fit 255 for securing a connecting rod 254 is disposed centrally of the rear side of the movable body 214, and an annular groove 257 for confining a seal ring 256 is disposed about the periphery of the movable body 214.

The connecting rod 254 functioning as an interlocking means 225 is a straight rod extending from the movable body 214 to the other direction axially of the casing 213. With one end of the connecting rod 254 fitted in the fit 255, it is secured centrally of the movable body 214. A piston 222 is centrally secured to the other end of the connecting rod 254. Thereby, the piston 222 is coaxially linked and connected to the movable body 214. The piston 222 is shaped into a disk. A fit 258 for identifying the connecting rod 254 is disposed centrally of the rear side of the piston 222, and an annular groove 260 for confining a seal ring 259 is disposed about the periphery of the piston 222.

Both seal rings 256 and 259 are composed of a rubber packing having an approximately V-formed section. As shown in FIG. 15, the seal ring 256 confined in the annular groove 257 of the movable body 214 is oriented such that its acting portion (the side to which the V-formed section opens) faces the storage chamber 212. This reliably prevents liquid leakage from the storage chamber 212. The seal ring 259 confined in the annular groove 260 of the piston 222 is oriented such that its acting portion faces the other end side (the side exposed to atmospheric pressure) of the cylinder 221. This reliably prevents the air from invading into a vacuum cylinder chamber 223.

The cylinder 221 is constructed by integrally closing one end side of a cylindrical peripheral wall 221a with a bottom 221b having a centrally located boss 261. A dome cover 263 having a centrally located vent 262 is secured to the opening on the other end of the peripheral wall 221a.

A rubber seal ring 264 is provided in the boss 261 of the bottom 221b. With the connecting rod 254 inserted into the boss 261, one end of the interior of the cylinder 221 is subject to airtight closure. A sealing 264 disposed in the boss 261 is composed of an approximately V-formed packing, as is the seal ring 256 of the movable body 214 and the seal ring 259 of the piston 222, and it is arranged such that its acting portion faces the casing 213 (the upper side as seen in FIG. 15). By virtue of the vent 262 of the cover 263, the other end side of the piston 222 is in communication with atmosphere.

Thus, with the other end of the cylinder 221 communicated to the atmosphere, the connecting rod 254 is inserted air-tight into the bottom 221b of the cylinder 221, and the piston 222 is inserted air-tight into the cylinder 221 for movement in an axial direction.

An external thread 265 projects from one end of the cylinder 221 and it is arranged such that when the external thread 265 is screwed into an internal thread formed in the opening on the other end of the casing 213, the cylinder 221 is coaxially connected to the casing 213. The external thread 265 and the internal thread 252 constitute a connecting means 266 between the cylinder 221 and the casing 213.

The connecting rod 254 is, as shown in FIG. 15, made slightly longer than the length in the axial direction of the casing 213, in order to locate the piston 222 outwardly axially (the lower side as seen in FIGS. 15 and 16) from the other end of the casing 213 when the movable body 214 is brought into engagement with the bottom wall 213b of the casing 213.

Therefore, when the external thread 265 of the cylinder 221 is screwed into the internal thread 252, with the movable body 214 located at the rearmost on the other side of the casing 213, a cylinder chamber 223 which has been maintained under vacuum between the bottom 221b of the cylinder 221 and the piston 222 is to be formed in the cylinder 221.

Figure 17:
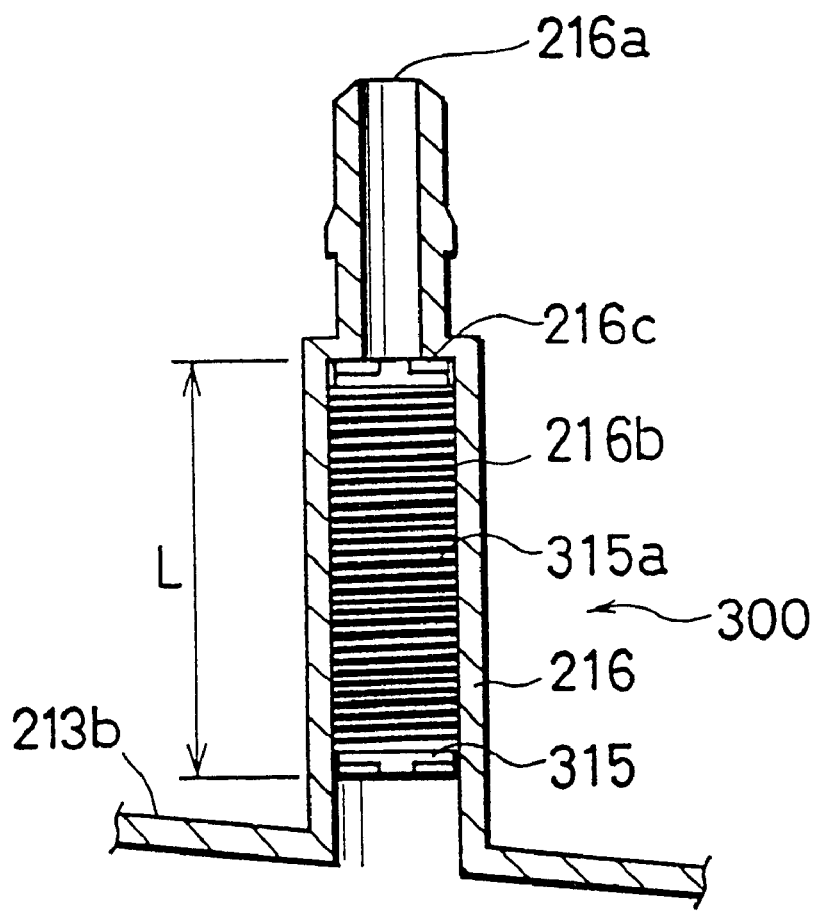
FIG. 17 is an enlarged view of a discharge regulation section incorporated in the liquid feeder of FIG. 15.

Referring now to FIG. 17, a discharge regulation section 300 will be described in detail. In the interior of an outlet part 216 where a discharge regulation section 300 will be arranged, a housing part 216b is disposed to define a cylindrical housing space. A cylindrical passage forming member 315 engages in the housing space of the housing part 216b. With the passage forming member 315 housed in the housing part 216b, its distal end is engaged to a step portion 216c. The housing part 216b has a fixing member (not shown) for engagement with the rear end of the passage forming member 315. Thus, the passage forming member 315 is housed and secured to the housing part 216b.

The passage forming member 315 is made of a resin material, e.g. plastic, by means of injection molding. A channel 315a having a sectional form, e.g., rectangle, triangle or semicircle, is spirally formed in the surface of the passage forming member 315. The outside diameter of the discharge forming member 315 is the same or slightly larger than the inside diameter of the housing part 216b. When the passage forming member 315 engages the housing part 216b in the above manner, its surface is brought into close contact with the inner surface of the outlet part 216 (the housing part 216b). Accordingly, a liquid flows through the storage chamber 212 to the housing part 216b and reaches one end side (the upper side as seen in FIG. 17) through the spiral channel 315a which functions as a liquid passage.

Operation of the liquid feeder so constructed will be described hereafter. As shown in FIG. 16, with the outlet 216a opened, the movable body 214 is pushed up from the opening on the other end of the casing 213 until it reaches the bottom wall 213b. Then, as shown in FIG. 15, the internal thread 265 of the cylinder 221 engages in the external thread 252 of the casing 213, and the cylinder 221 is axially rotated relative to the casing 213 in the direction for screwing. Thereby, the cylinder 221 is screwed and connected to the other end of the casing 213.

At this time, since the connecting rod 254 is made slightly longer than the casing 213, the piston 222 moves away from the bottom 221b of the cylinder 221 upon completion of engagement with the casing 213 of the cylinder 221. As a result, a flat vacuum cylinder chamber 223, as defined by the bottom 221b and the piston 222, is formed on one end side in the cylinder 221.

Figure 18:
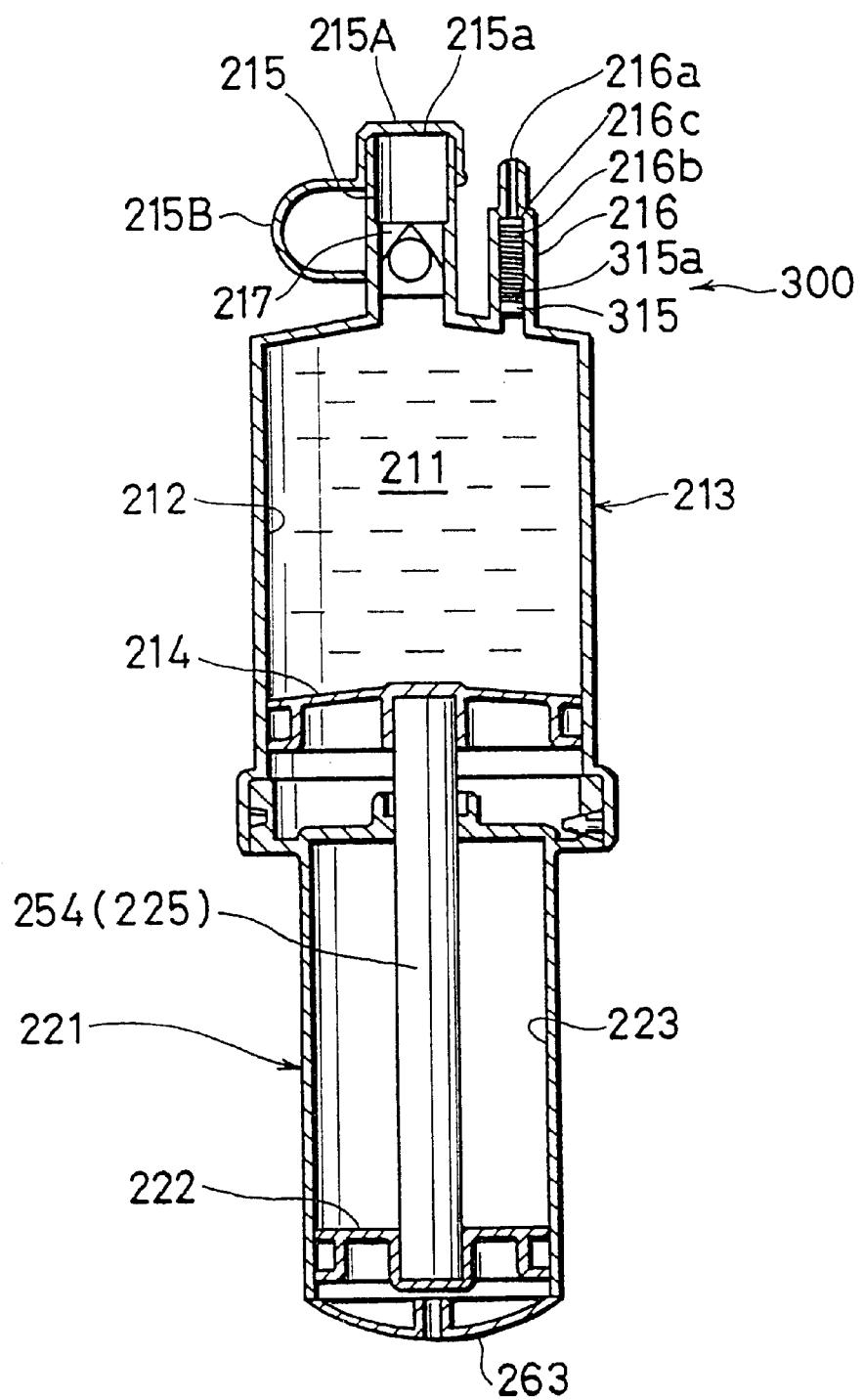
FIG. 18 is a diagram showing operation of the liquid feeder of FIG. 15.

Then, with the outlet 216a closed, as a liquid is forced through the inlet 215a by a syringe or the like, the movable body 214 moves to the other end side (downward) of the casing 213 to increase the volume of the storage chamber 212 to be formed in front of the movable body 214. At the same time, the piston 222 also moves to the other end side of the cylinder 221, so that the volume of the above-mentioned vacuum cylinder chamber 223 is gradually increased. Then, as shown in FIG. 18, preparation for injection is completed when the piston 222 reaches the vicinity of the cover 263. In FIG. 18, reference numeral 211 designates the liquid thus stored in the storage chamber 212.

Thereafter, when the inlet 215a is covered with the cap 215A and the outlet 216a is opened, the liquid 211 stored in the storage chamber 212 is introduced into the outlet 216a via the channel 315a functioning as a passage. The sectional form and length of the channel 315a are determined in advance at the time of designing the liquid feeder. Since the pipe loss of a passage formed by the channel 315a has a predetermined value corresponding to the sectional area and length, the liquid flows through the outlet 216a at a discharge according to the pipe loss. The liquid discharged through the outlet 216a is then injected into the patient's body via a tube (not shown) connected to the outlet 216a.

As stated above, in the liquid feeder according to this preferred embodiment, it is arranged such that the discharge regulation section 300 is incorporated in the outlet part 216 of the casing (the device body) 213 and the discharge of liquid flowing through the outlet 216a is always regulated at a predetermined value. Therefore, compared to the conventional cases where a liquid feeder and a discharge regulator are provided separately and independently and both are connected together by a tube, this liquid feeder enables a simplified arrangement for liquid injection to the patient and also lowers the cost. In addition, this liquid feeder eliminates the need for work which has been essential for liquid injection, namely the work of connecting a liquid feeder and a discharge regulator by using a tube or the like, thus improving the operating performance of liquid injection.

Although in this embodiment, the discharge regulation section 300 is incorporated in the liquid feeder constructed in combination with the casing 213 and the cylinder 221, this invention is applicable to any well-known liquid feeders, such as power syringe pumps and balloon infusers. That is, the same effect as the foregoing preferred embodiments is obtained by incorporating the discharge regulation section 300 in the outlet part of the liquid feeder.

Although in this embodiment, the passage forming member 315 constituting the discharge regulation section 300 is made of a resin material, e.g., plastic, it may be made by machining other material, e.g., glass or metals. The molding method is not limited to injection molding and any other known molding methods may be employed. The channel 315a is provided in the surface of the columnar passage forming member 315, the channel forming member 315 may have an arbitrary sectional form. For instance, solid or hollow columnar ones having a columnar, multi-prismatic or cylindrical shape can be adopted, provided that the surface of the passage forming member 315 is brought into close contact with the inner surface of the casing 213 (the outlet part 216) to introduce a liquid toward the outlet 216a along the channel 315a.

Although in this embodiment, the spiral channel 315a is provided in the surface of the channel forming member 315, the channel 315 is merely required to wind such as to have a length sufficiently longer than the whole length L (see FIG. 17) of the passage forming member 315, and it may be formed windingly in random fashion.

Although in this embodiment, the discharge regulation section 300 is constructed by the discharge regulator substantially according to the first preferred embodiment (FIG. 1), it may be constructed by any one of the discharge feeders according to the second to fourth preferred embodiments.

Although in this embodiment, the discharge regulation section 300 is attained by using, as a liquid passage, the channel 315a provided spirally in the surface of the channel forming member 315, and setting the pipe loss of this passage in advance, the arrangement of the discharge regulation section is not limited thereto. For example, discharge regulation can be effected by using, as a passage, a glass tube of fine diameter or a tube of fine diameter made of polyvinyl chloride, disposing it in the outlet part 216, and suitably setting the pipe loss of the passage. However, compared to the case using the glass tube or tube of fine diameter as a passage, when the channel 315a is used as a passage, as is the above embodiment, the following advantages are obtained.

Description will now be given of the case where the passage of a discharge regulation section is formed by a tube of fine diameter. The pipe loss of the passage is determined by inside diameter and length. Therefore, to control the flow rate, in general, the pipe loss of the tube of fine diameter is suitably set by adjusting its length. In this case, however, if a tube of fine diameter having a length corresponding to a predetermined pipe loss is used as it is, the desired pipe loss may not be always obtained because a certain variation may occur in the inside diameter of tubes of fine diameter. To this end, the following operations are performed to set a pipe loss. Firstly, a tube of fine diameter with a length corresponding to a pipe loss is prepared, and a liquid is actually used to measure its pipe loss (flow rate), thereby inspecting whether it is a predetermined pipe loss or not. As a result, when the obtained value deviates from the predetermined value, the length of the tube is altered and its pipe loss is measured to check whether it is the predetermined value or not. It is necessary to repeat these operations with respect to each passage. This results in one of the factors which can increase the cost of manufacture.

Alternatively, it is conceived to suppress the variation in the inside diameters of tubes of fine diameter by relatively increasing the inside diameter. In this case, to obtain a predetermined pipe loss, it is necessary to increase the length of a tube of fine diameter as its inside diameter increases. This increases the size of discharge regulators. In addition, when a tube of fine diameter is housed in a casing, the tube may get bent to cause poor or no flow of liquid, making it difficult to perform discharge regulation.

On the other hand, in the case where the channel 315a provided spirally in the surface of the passage forming member 315 functions as a liquid passage, the following effect is obtained. Specifically, the well-known methods, e.g., injection molding, can be used in manufacturing the passage forming member 315 of plastic which has the channel 315a on its surface, and the sectional form and length of the channel 315a can be formed at high precision in accordance with the design. Hence, a desired pipe loss is obtained at a time by designing in advance the sectional form and length of the channel 315a so as to correspond to the pipe loss. Particularly, with injection molding, mass production of the passage forming member 315 of identical pipe loss can be effected only by preparing a mold corresponding to the pipe loss, thereby leading to a considerable reduction in manufacturing cost.

In addition, the channel 315a serving as a passage is spirally provided in the surface of the passage forming member 315 such that the channel 315a is sufficiently longer than the whole length L of the passage forming member 315 (see FIG. 17). Therefore, the sectional area of the channel 315a can be increased by the amount of the ensured sufficient length, and the passage (the channel 315a) hardly becomes clogged. Also, a greater sectional area of the channel 315a further facilitates molding of the channel forming member 315 and further improves the precision.

Since the channel 315a is arranged to function as a passage, passages can be concentrated at a narrow region and thus leads to a compact device, as compared to the prior art employing a tube of fine diameter as a passage.

As described above, a liquid discharge regulator includes one or more passage forming members housed in a casing having liquid inlet and outlet parts. A liquid is introduced from the inlet part to the outlet part via a passage formed by the casing and the passage forming member, thereby regulating the discharge of the liquid flowing through the outlet part. The surface of the passage forming member is formed with a channel, which functions as a liquid passage. The channel can be readily formed with high precision in accordance with the design by the recent machining technique. Accurate setting of the pipe loss to be formed by the channel is attainable only by designing its sectional form and length appropriately. Hence, the passage of a desired pipe loss can be obtained without repeating a sequence of steps of: measurement; inspection; and then correction, in order to set a pipe loss as has been conventional.

The channel may be formed windingly to have a length sufficiently longer than the whole length of the passage forming member. This permits a longer channel and ensures a pipe loss suitable for liquid discharge regulation.

The passage forming member may be of a columnar shape, and its peripheral surface may have a channel in spiral form.

There may be provided a plurality of liquid passages by disposing a plurality of housing parts to house a passage forming member in the casing and housing a plurality of liquid forming members of different pipe losses in their respective housing parts, as well as a passage switching means to control switching of the liquid passages, such that the discharge of liquid flowing through the outlet part is regulatable by selectively switching the liquid passages with the passage switching means.

A plural-stage regulation of the discharge of liquid flowing through the outlet part is attained by virtue of the plurality of liquid passages which are obtained by disposing the plurality of housing parts to house the passage forming member in the casing and confining the plurality of passage forming members of different pipe losses in their respective housing parts, as well as the passage switching means to control switching of the passages.

The passage switching means may be disposed, for example, between the housing part and the inlet part or the outlet part.

There may be disposed a bypass passage which provides communication between the inlet part and the outlet part in the casing, and a bypass passage switching means to control switching of the bypass passage, such that when the bypass passage is opened, a liquid flows through the outlet part in an amount sufficiently greater than the flow rate of the passage formed by the passage forming member.

Thanks to the bypass passage providing communication between the inlet and outlet parts in the casing and the bypass passage switching means to control switching of the bypass passage, when the bypass passage is opened, a liquid flows through the outlet part in an amount sufficiently greater than the flow rate of the passage formed by the passage forming member. This permits a sharp increase in the liquid discharge in response to the change of the patient's condition and the efficacy of chemical liquids.

The passage forming member may be constructed such that it is movable relative to the housing part and the position of the channel opposite one of the inlet and outlet parts can be changed by relative movement of the passage forming member. With this construction, the pipe loss of the passage can be changed by correcting the length of the channel from the aforesaid opposite position to the other, namely the length of the passage.

The discharge of liquid flowing through the outlet part can be changed continuously by virtue of the arrangement that the position of the channel opposite one of the inlet and outlet parts is changed by a relative movement of the passage forming member with respect to the housing part, and the pipe loss of the passage is changed by correction of the length of the channel from the opposed position to the other, namely the length of the passage.

The a bypass passage providing communication between the inlet and outlet part is disposed in the casing and the bypass passage is subjected to switching control according to the relative position of the passage forming member to the housing member, whereby, when the bypass passage is opened, a liquid flows through the outlet part in an amount sufficiently greater than the flow rate of the passage formed by the passage forming member.

Thanks to the arrangement that the bypass passage providing communication between the inlet and outlet parts is disposed in the casing and the bypass passage is subjected to switching control according to the relative position of the passage forming member to the housing member, when the bypass passage is opened, a liquid flows from the outlet part in an amount sufficiently greater than the flow rate of the passage formed by the passage forming member. This permits a sharp increase in the liquid discharge in response to the change of the patient's condition and the efficacy of chemical liquids.

The passage forming member may be of a hollow columnar shape, and a hollow region may serve as a bypass passage.

There may be provided, in the passage forming member, a regulation region which closes one of the inlet and outlet parts to regulate liquid communication from the inlet part to the outlet part. In this construction, the outflow of liquid can be stopped by the regulation region.

The diameter of the liquid passage from the inlet part to the channel may become smaller as approaching from the inlet part to the channel. When a liquid, e.g., physiological salt solution, is allowed to flow, a sharp reduction in passage diameter might cause the problem that part of the liquid is liable to crystallize at discontinuous portions of the passage diameter and the passage becomes clogged by crystalline. It is, however, possible to prevent such a crystallization by gradually reducing the diameter of a passage according to the invention.

The feature that the diameter of the liquid passage from the inlet part to the channel becomes smaller as it approaches from the inlet part to the channel is effective in preventing a portion of liquid from being crystallized, thus free from a clogging of the passage.

The passage forming member may be made of plastic, and its manufacture by means of injection molding facilitates accurate formation of the sectional form and length of the channel.

A liquid feeder with which liquid stored in a main body of the feeder is delivered outside through an outlet of an output part disposed on the distal end of the main body, incorporates, in the outlet part, a discharge regulation section which introduces a liquid from the interior of the main body to the outlet and regulates the discharge of the liquid flowing to the outlet.

The discharge regulation section disposed in the outlet part of the liquid feeder introduces a liquid from the interior of the feeder to the outlet and also regulates the discharge of the liquid flowing through the outlet. Thus, compared to the conventional cases where a liquid feeder and a discharge regulator are provided separately and independently and both are connected together by a tube, the liquid feeder has a simplified arrangement for liquid injection to the patient and also lowers the cost of manufacture. In addition, the liquid feeder eliminates the need for work which has been essential for liquid injection, namely the work of connecting a liquid feeder and a discharge regulator by using a tube or the like, thus increasing the operating performance of liquid injection.

The above discharge regulation section may be constituted by any one of liquid discharge regulators as set forth above. Accordingly, the effect obtained by the discharge regulator is attained in addition to the effect obtained by the liquid feeder.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

What is claimed is:

1. A liquid discharge regulator comprising:
    a casing having a liquid inlet part, a liquid outlet part, and a plurality of housing parts;
    a plurality of passage forming members each formed with a channel in a surface thereof, the surface of each passage forming member coming into contact with an inner surface of the casing to define a passage for introducing a liquid from the inlet part to the outlet part, the passage forming members regulate the discharge of the liquid from the outlet part, the plurality of passage forming members of different pipe losses being housed in their respective housing parts to obtain the plurality of liquid passages; and
    a passage switcher for switching the liquid passages such that the discharge of the liquid flowing through the outlet part is regulated by selectively switching the passage switcher.

2. The liquid discharge regulator according to claim 1, wherein the passage switcher is disposed between the housing part and the inlet or the outlet part.

3. A liquid discharge regulator according to claim 1, wherein the channel is formed windingly to have a length sufficiently longer than an overall length of the passage forming member.

4. A liquid discharge regulator according to claim 1, wherein the passage forming member is of a columnar shape and the channel is spirally formed in a peripheral surface thereof.

5. A liquid discharge regulator according to claim 1, wherein the diameter of a liquid passage from the inlet part to the channel becomes smaller when approaching from the inlet part to the channel.

6. A liquid discharge regulator according to claim 1, wherein the passage forming member is formed of a plastic by infection molding.

7. A liquid discharge regulator comprising:
    a casing having a liquid inlet part and a liquid outlet part, the casing having a cylindrical chamber;
    a passage forming member having the form of a cylinder and being movable along an axial direction of the cylindrical chamber, the passage forming member being formed with a channel in a surface thereof, the surface of the passage forming member coming into contact with an inner surface of the cylindrical chamber of the casing to define a passage for introducing a liquid from the inlet part to the outlet part and to regulate the discharge of the liquid from the outlet part;
    a controller rotatably mounted in the casing but being unmovable with respect to the axial direction, the controller being operatively engaged with the passage forming member;
    a movement conversion mechanism for converting a rotational movement of the controller into an axial movement of the passage forming member relative to the casing to change a position of the channel opposite to one of the inlet and outlet parts for correction of the length of the channel from one position to another.

8. The liquid discharge regulator according to claim 7, further comprising a bypass passage disposed in the casing for providing communication between the inlet part and the outlet part, the bypass passage being subjected to switching control in response to the position of the passage forming member relative to the housing part, such that when the bypass passage is opened, a liquid is allowed to discharge through the outlet part in an amount sufficiently greater than the flow rate of the passage formed by the passage forming member.

9. The liquid discharge regulator according to claim 8, wherein the passage forming member is of a hollow cylinder, having the channel spirally formed in a peripheral surface thereof and a hollow region functioning as the bypass passage.

10. The liquid discharge regulator according to claim 7, further comprising a regulation region located in a portion of the passage forming member, the regulation region closing one of the inlet and outlet parts to regulate liquid communication from the inlet part to the outlet part.

11. A liquid discharge regulator according to claim 7, wherein the movement conversion mechanism includes:
- a force transmission means for transmitting the rotational force of the controller to the passage forming member; and
- a retaining means for keeping the passage forming member from being rotated by the rotational force of the controller.

* * * * *